(12) United States Patent
Li et al.

(10) Patent No.: US 12,398,153 B2
(45) Date of Patent: Aug. 26, 2025

(54) SPIRO COMPOUND SERVING AS ERK INHIBITOR, AND APPLICATION THEREOF

(71) Applicant: D3 BIO (WUXI) CO., LTD., Wuxi (CN)

(72) Inventors: Yi Li, Shanghai (CN); Ning Liu, Shanghai (CN); Tao Yu, Shanghai (CN); Chengde Wu, Shanghai (CN); Jian Li, Shanghai (CN); Shuhui Chen, Shanghai (CN)

(73) Assignee: D3 BIO (WUXI) CO., LTD., Wuxi (CN)

( * ) Notice: Subject to any disclaimer, the term of this patent is extended or adjusted under 35 U.S.C. 154(b) by 702 days.

(21) Appl. No.: 17/782,850

(22) PCT Filed: Dec. 7, 2020

(86) PCT No.: PCT/CN2020/134277
§ 371 (c)(1),
(2) Date: Jun. 6, 2022

(87) PCT Pub. No.: WO2021/110168
PCT Pub. Date: Jun. 10, 2021

(65) Prior Publication Data
US 2023/0044606 A1    Feb. 9, 2023

(30) Foreign Application Priority Data

| Dec. 6, 2019 | (CN) | 201911244788.X |
| Dec. 10, 2019 | (CN) | 201911257998.2 |
| Feb. 20, 2020 | (CN) | 202010106897.1 |
| Sep. 30, 2020 | (CN) | 202011068937.4 |
| Dec. 3, 2020 | (CN) | 202011410488.7 |

(51) Int. Cl.
  *C07D 513/20* (2006.01)
  *A61P 1/00* (2006.01)
  *A61P 35/00* (2006.01)

(52) U.S. Cl.
  CPC ............. *C07D 513/20* (2013.01); *A61P 1/00* (2018.01); *A61P 35/00* (2018.01)

(58) Field of Classification Search
  None
  See application file for complete search history.

(56) References Cited

FOREIGN PATENT DOCUMENTS

| CN | 107108648 A | 12/2015 |
| CN | 107074874 A | 8/2017 |
| RU | 2525389 C2 | 8/2014 |
| WO | WO 2019/223632 A1 | 11/2019 |
| WO | WO 2020/228817 A1 | 11/2020 |

OTHER PUBLICATIONS

Kummerer et al., Pharmaceuticals in the Environment. Annu Rev Environ Resour. Aug. 18, 2010;35:57-75.
Yaeger et al., "Targeting Alterations in the RAF-MEK Pathway," Cancer Discov. (Mar. 2019); 9(3):329-341.

*Primary Examiner* — Bong-Sook Baek
(74) *Attorney, Agent, or Firm* — Fenwick & West LLP

(57) ABSTRACT

A Spiro compound serving as an ERK inhibitor, and an application thereof in preparing a drug for treating an ERK-related disease. The present invention specifically relates to a compound represented by formula (III) or a pharmaceutically acceptable salt thereof.

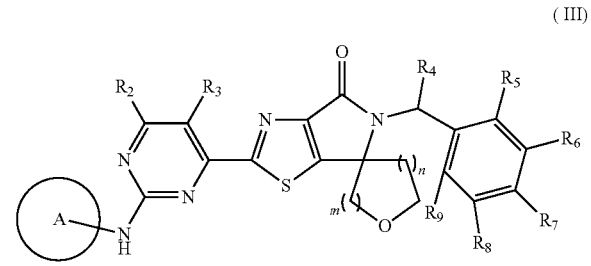

(III)

14 Claims, 1 Drawing Sheet

SPIRO COMPOUND SERVING AS ERK INHIBITOR, AND APPLICATION THEREOF

The present application is a United States National Phase under 35 U.S.C. § 371 of International Application No. PCT/CN2020/134277, filed Dec. 7, 2020, which claims the priority of: CN201911244788.X, filed on Dec. 6, 2019; CN201911257998.2, filed on Dec. 10, 2019; CN202010106897.1, filed on Feb. 20, 2020; CN202011068937.4, filed on Sep. 30, 2020; and CN202011410488.7, filed on Dec. 3, 2020.

FIELD OF THE INVENTION

The present disclosure relates to a spiro compound as an ERK inhibitor, and use thereof in the manufacture of a medicament for treating diseases related to ERK. Specifically, the present disclosure relates to a compound represented by formula (III) or a pharmaceutically acceptable salt thereof.

BACKGROUND OF THE INVENTION

Ras/Raf/MEK/ERK pathway is a classical mitogen activated protein kinase (MAPK) signaling cascade pathway, is involved in the signal transduction of various growth factors, cytokines, mitogens and hormone receptors after activation, and is one of the most important signal transduction pathways for controlling cell growth, differentiation and survival.

Studies have shown that abnormal activation of Ras/Raf/MEK/ERK pathway caused by mutation or amplification is a determinant of various cancers. In human tumors, the incidence of RAS mutation is about 22%, the incidence of BRAF mutation is about 7%, and the incidence of MEK mutation is about 1%. Therefore, key node proteins on this pathway have become important targets for the treatment of cancers (*Cancer Discov.* 2019, 9, 329-341). Currently, a number of BRAF inhibitors and MEK1/2 inhibitors, as well as their combination regimens, have been approved by the US FDA for the treatment of melanoma, BRAFV600E mutant non-small cell lung cancer and other cancers. However, the use of BRAF and MEK inhibitors for these upstream nodes can rapidly lead to a problem of drug resistance due to mutation or pathway reactivation, greatly limiting their clinical application.

Extracellular regulated protein kinases (ERK) (especially ERK1 and ERK2 kinases) are major players and downstream key nodes in the Ras/Raf/MEK/ERK pathway, and their over-activation can be found in many human cancers. ERK, as the terminal signaling kinase of this pathway, has not yet been found to have mutations that lead to drug resistance. Therefore, a drug targeting ERK kinase is expected to overcome the problem of drug resistance caused by the treatment with upstream target inhibitors, and become a more potential therapeutic strategy. But so far, research on ERK inhibitors is still in the clinical phase, and no ERK inhibitors have been approved for marketing as drugs.

In summary, there is an urgent need to develop a safe and effective ERK inhibitor drug to meet the need of treatment of a tumor.

SUMMARY OF THE INVENTION

The present disclosure provides a compound of formula (III) or a pharmaceutically acceptable salt thereof,

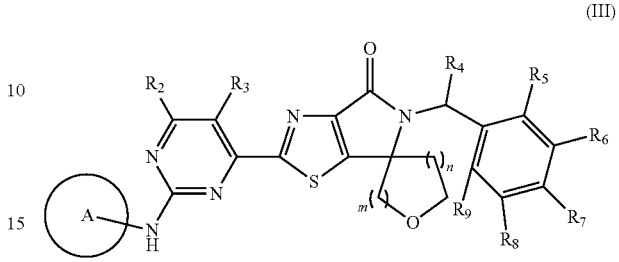

wherein
n is 0 or 1;
m is 1 or 2;
ring A is

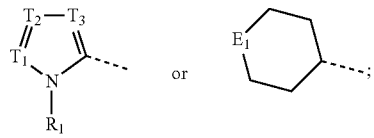

$T_1$, $T_2$ and $T_3$ are each independently selected from N and CH;
$E_1$ is O, S or NH;
$R_1$ is selected from H and $C_{1-3}$ alkyl, wherein the $C_{1-3}$ alkyl is optionally substituted by 1, 2 or 3 $R_a$;
$R_2$ and $R_3$ are each independently selected from H, F, Cl, Br, I, OH, CN, $NH_2$ and $C_{1-3}$ alkyl, wherein the $C_{1-3}$ alkyl is optionally substituted by 1, 2 or 3 $R_b$;
$R_4$ is H;
$R_5$, $R_6$, $R_7$, $R_8$ and $R_9$ are each independently selected from H, F, Cl, Br, I, OH, CN, $NH_2$ and $C_{1-3}$ alkyl, wherein the $C_{1-3}$ alkyl is optionally substituted by 1, 2 or 3 $R_c$;
$R_a$, $R_b$ and $R_c$ are each independently selected from F, Cl, Br, I, OH, CN and $NH_2$.

In some embodiments of the present disclosure, the above-mentioned $R_1$ is selected from H and $CH_3$, wherein the $CH_3$ is optionally substituted by 1, 2 or 3 $R_a$, and other variables are as defined in the present disclosure.

In some embodiments of the present disclosure, the above-mentioned $R_1$ is $CH_3$, and other variables are as defined in the present disclosure.

In some embodiments of the present disclosure, the above-mentioned $R_2$ and $R_3$ are each independently selected from H, F, Cl, Br, I, OH, CN, $NH_2$ and $CH_3$, wherein the $CH_3$ is optionally substituted by 1, 2 or 3 $R_b$, and other variables are as defined in the present disclosure.

In some embodiments of the present disclosure, the above-mentioned $R_2$ and $R_3$ are each independently selected from H and $CH_3$, and other variables are as defined in the present disclosure.

In some embodiments of the present disclosure, the above-mentioned $R_2$ and $R_3$ are each independently H, and other variables are as defined in the present disclosure.

In some embodiments of the present disclosure, the above-mentioned $R_5$, $R_6$, $R_7$, $R_8$ and $R_9$ are each independently selected from H, F, Cl, Br, I, OH, CN, $NH_2$, $CH_3$ and —CH$_2$—CH$_3$, wherein the CH$_3$ and —CH$_2$—CH$_3$ are optionally substituted by 1, 2 or 3 R$_c$, and other variables are as defined in the present disclosure.

In some embodiments of the present disclosure, the above-mentioned R$_5$, R$_6$, R$_7$, R$_8$ and R$_9$ are each independently selected from H, F, Cl, Br, I, OH, CN and NH$_2$, and other variables are as defined in the present disclosure.

In some embodiments of the present disclosure, the above-mentioned structural moiety

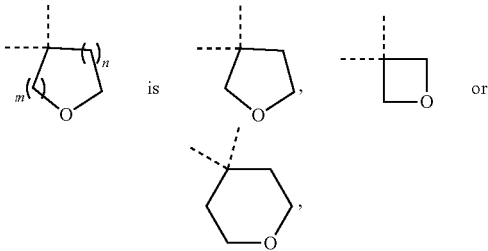

and other variables are as defined in the present disclosure.

In some embodiments of the present disclosure, the above-mentioned structural moiety

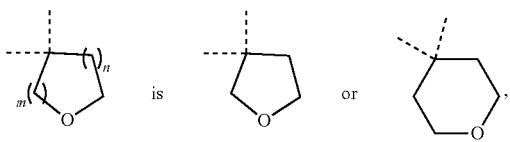

and other variables are as defined in the present disclosure.

In some embodiments of the present disclosure, the above-mentioned ring A is

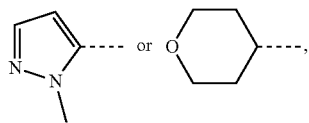

and other variables are as defined in the present disclosure.

The present disclosure provides a compound of formula (I) or a pharmaceutically acceptable salt thereof,

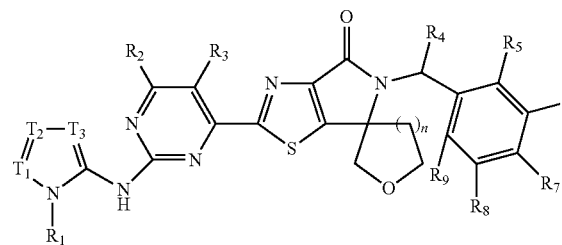

wherein n is 0 or 1;

T$_1$, T$_2$ and T$_3$ are each independently selected from N and CH;

R$_1$ is selected from H and C$_{1-3}$ alkyl, wherein the C$_{1-3}$ alkyl is optionally substituted by 1, 2 or 3 R$_a$;

R$_2$ and R$_3$ are each independently selected from H, F, Cl, Br, I, OH, CN, NH$_2$ and C$_{1-3}$ alkyl, wherein the C$_{1-3}$ alkyl is optionally substituted by 1, 2 or 3 R$_b$;

R$_4$ is H;

R$_5$, R$_6$, R$_7$, R$_8$ and R$_9$ are each independently selected from H, F, Cl, Br, I, OH, CN, NH$_2$ and C$_{1-3}$ alkyl, wherein the C$_{1-3}$ alkyl is optionally substituted by 1, 2 or 3 Re;

R$_a$, R$_b$ and R$_c$ are each independently selected from F, Cl, Br, I, OH, CN and NH$_2$.

In some embodiments of the present disclosure, the above-mentioned R$_1$ is selected from H and CH$_3$, wherein the CH$_3$ is optionally substituted by 1, 2 or 3 R$_a$, and other variables are as defined in the present disclosure.

In some embodiments of the present disclosure, the above-mentioned R$_1$ is CH$_3$, and other variables are as defined in the present disclosure.

In some embodiments of the present disclosure, the above-mentioned R$_2$ and R$_3$ are each independently selected from H, F, Cl, Br, I, OH, CN, NH$_2$ and CH$_3$, wherein the CH$_3$ is optionally substituted by 1, 2 or 3 R$_b$, and other variables are as defined in the present disclosure.

In some embodiments of the present disclosure, the above-mentioned R$_2$ and R$_3$ are each independently H, and other variables are as defined in the present disclosure.

In some embodiments of the present disclosure, the above-mentioned R$_5$, R$_6$, R$_7$, R$_8$ and R$_9$ are each independently selected from H, F, Cl, Br, I, OH, CN, NH$_2$, CH$_3$ and —CH$_2$—CH$_3$, wherein the CH$_3$ and —CH$_2$—CH$_3$ are optionally substituted by 1, 2 or 3 R$_c$, and other variables are as defined in the present disclosure.

In some embodiments of the present disclosure, the above-mentioned R$_5$, R$_6$, R$_7$, R$_8$ and R$_9$ are each independently selected from H, F, Cl, Br, I, OH, CN and NH$_2$, and other variables are as defined in the present disclosure.

The present disclosure also includes some embodiments that are obtained by combining any of the above-mentioned variables.

In some embodiments of the present disclosure, the above-mentioned compound or a pharmaceutically acceptable salt thereof is disclosed, wherein the compound is selected from

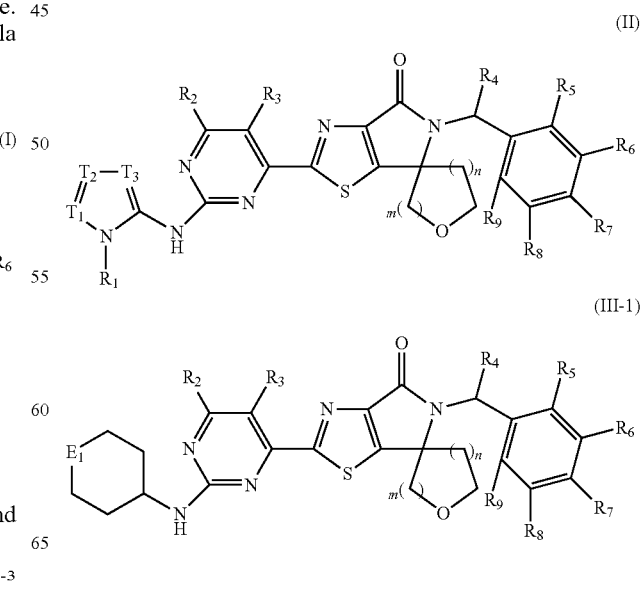

wherein m, n, $E_1$, $T_1$, $T_2$, $T_3$, $R_1$, $R_2$, $R_3$, $R_4$, $R_5$, $R_6$, $R_7$, $R_8$ and $R_9$ are as defined in the present disclosure.

In some embodiments of the present disclosure, the above-mentioned compound or a pharmaceutically acceptable salt thereof is disclosed, wherein the compound is selected from

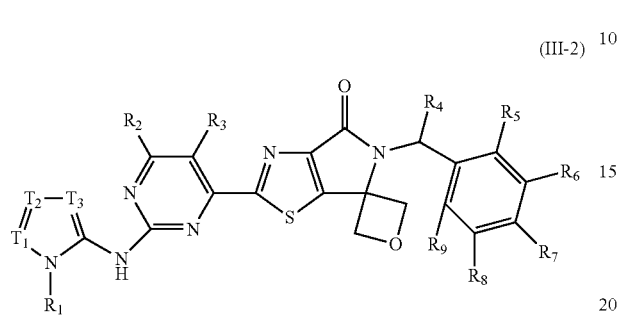
(III-2)

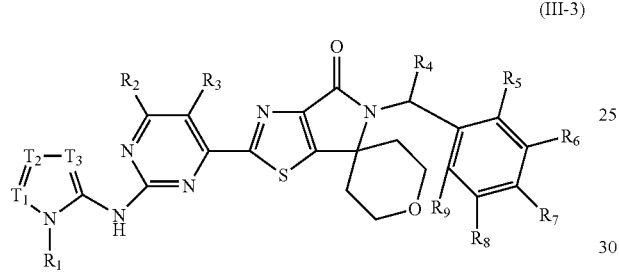
(III-3)

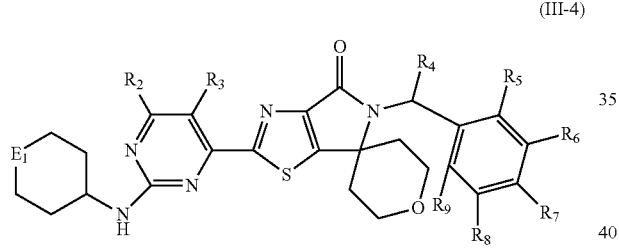
(III-4)

wherein $R_1$, $R_2$, $R_3$, $R_4$, $R_5$, $R_6$, $R_7$, $R_8$, $R_9$, $E_1$, $T_1$, $T_2$ and $T_3$ are as defined in the present disclosure.

In some embodiments of the present disclosure, the above-mentioned compound or a pharmaceutically acceptable salt thereof is disclosed, wherein the compound is selected from

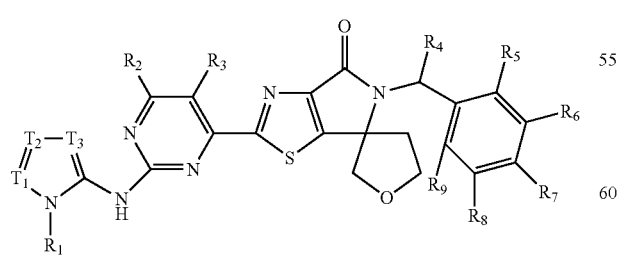
(II-1)

wherein $T_1$, $T_2$, $T_3$, $R_1$, $R_2$, $R_3$, $R_4$, $R_5$, $R_6$, $R_7$, $R_8$ and $R_9$ are as defined in the present disclosure.

In some embodiments of the present disclosure, the above-mentioned compound or a pharmaceutically acceptable salt thereof is disclosed, wherein the compound is selected from

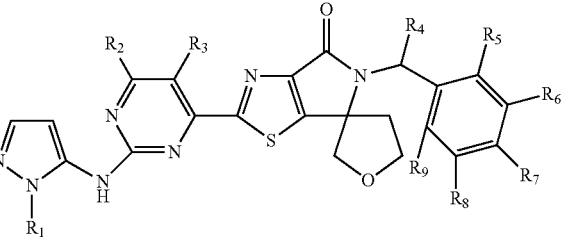
(I-1)

wherein $R_1$, $R_2$, $R_3$, $R_4$, $R_5$, $R_6$, $R_7$, $R_8$ and $R_9$ are as defined in the present disclosure.

The present disclosure also provides a compound represented by the following formula or a pharmaceutically acceptable salt thereof,

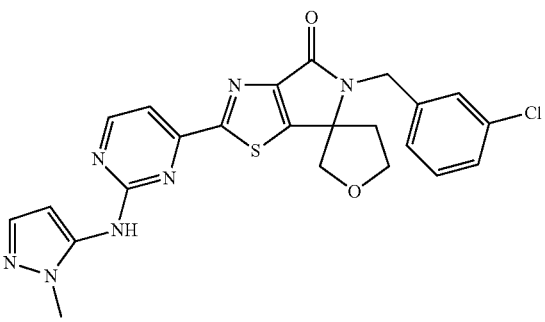

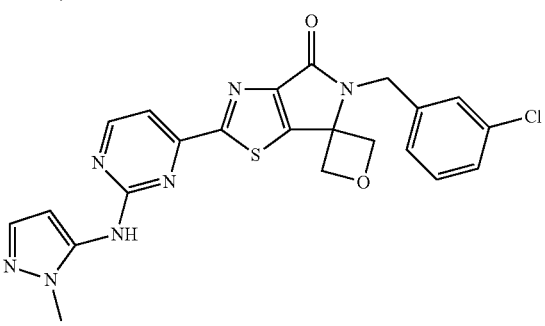

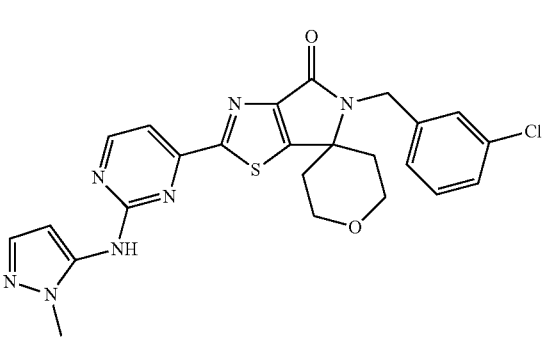

-continued

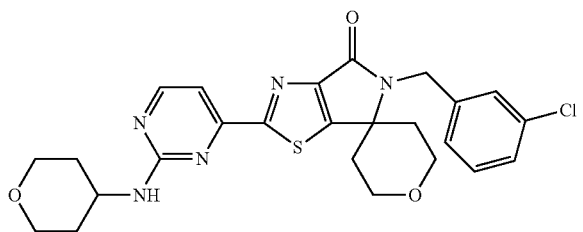

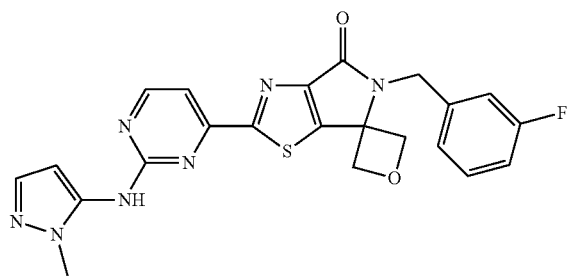

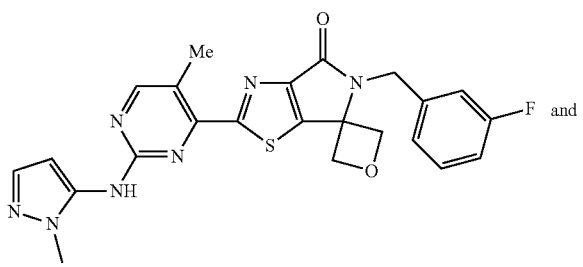

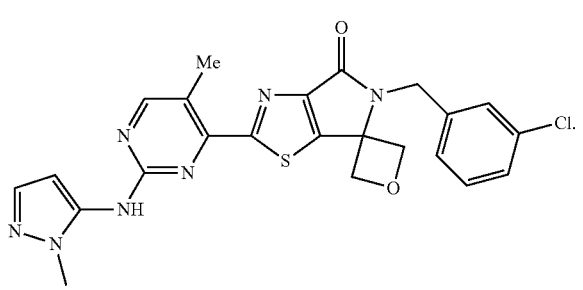 [SMILES: Cc1cnc(Nc2ccnn2C)nc1-c1nc2c(s1)C1(COC1)N(Cc1cccc(Cl)c1)C2=O]

In some embodiments of the present disclosure, the above-mentioned compound or a pharmaceutically acceptable salt thereof is disclosed, wherein the compound is selected from

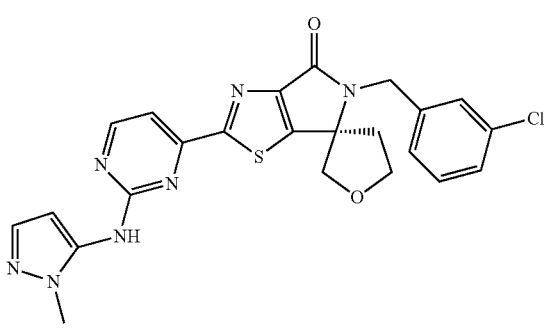

-continued

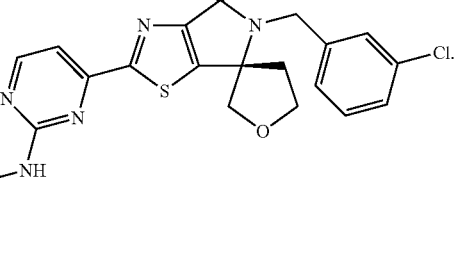

The present disclosure also provides use of the above-mentioned compound or an isomer or a pharmaceutically acceptable salt thereof in the manufacture of a medicament for treating diseases related to ERK.

Technical Effect

The compounds of the present disclosure exhibit excellent inhibitory activity to ERK2 kinase and HT29 cell proliferation. Meanwhile, the compounds of the present disclosure exhibit excellent oral exposure and bioavailability. Moreover, the compounds of the present disclosure can significantly inhibit the growth of tumor. During the administration, the body weight of animals is not observed to decrease significantly, and the tolerance is good.

Definition and Term

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" means a salt of compounds disclosed herein that is prepared by reacting the compound having a specific substituent disclosed herein with a relatively non-toxic acid or base. When compounds disclosed herein contain a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium or similar salts. When compounds disclosed herein contain a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

Compounds disclosed herein may be present in a specific geometric or stereoisomeric form. The present disclosure contemplates all such compounds, including cis and trans isomers, (−)- and (+)-enantiomers, (R)- and (S)-enantiomers, diastereoisomer, (D)-isomer, (L)-isomer, and a racemic mixture and other mixtures, for example, a mixture enriched in enantiomer or diastereoisomer, all of which are encompassed within the scope disclosed herein. The substituent such as alkyl may have an additional asymmetric carbon atom. All these isomers and mixtures thereof are encompassed within the scope disclosed herein.

Unless otherwise specified, the term "enantiomer" or "optical isomer" refers to stereoisomers that are in a mirrored relationship with each other.

Unless otherwise specified, the term "cis-trans isomer" or "geometric isomer" is produced by the inability of a double bond or a single bond between ring-forming carbon atoms to rotate freely.

Unless otherwise specified, the term "diastereomer" refers to a stereoisomer in which two or more chiral centers of are contained in a molecule and is in a non-mirrored relationship between molecules.

Unless otherwise specified, "(+)" means dextroisomer, "(−)" means levoisomer, and "(±)" means racemate.

Unless otherwise specified, a wedged solid bond (◂) and a wedged dashed bond (◂) indicate the absolute configuration of a stereocenter; a straight solid bond (◂) and a straight dashed bond (◂) indicate the relative configuration of a stereocenter; a wavy line (◂) indicates a wedged solid bond (◂) or a wedged dashed bond (◂) or a wavy line (◂) indicates a straight solid bond (◂) and a straight dashed bond (◂).

Unless otherwise specified, when a double bond structure such as a carbon-carbon double bond, a carbon-nitrogen double bond, and a nitrogen-nitrogen double bond is present in a compound, and each atom on the double bond is attached to two different substituents (in the double bond containing a nitrogen atom, a pair of lone pair electrons on the nitrogen atom is considered as one of the substituents to which it is attached), the compound represents (Z) isomer, (E) isomer, or a mixture of two isomers of the compound, if the atoms on the double bond in the compound are attached to their substituents by a wavy line (◂). For example, the compound having following formula (A) means that the compound is present as a single isomer of formula (A-1) or formula (A-2) or as a mixture of two isomers of formula (A-1) and formula (A-2); and the compound having following formula (B) means that the compound is present as a single isomer of formula (B-1) or formula (B-2) or as a mixture of two isomers of formula (B-1) and formula (B-2). The compound having following formula (C) means that the compound is present as a single isomer of formula (C-1) or formula (C-2) or as a mixture of two isomers of formula (C-1) and formula (C-2).

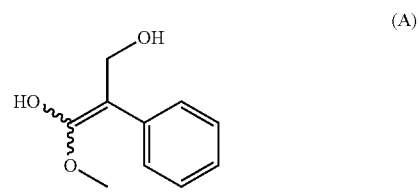
(A)

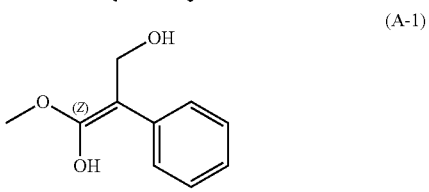
(A-1)

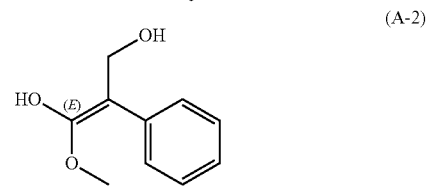
(A-2)

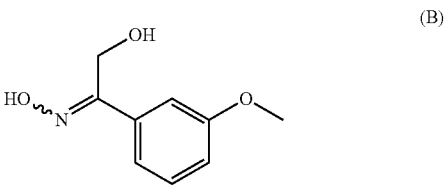
(B)

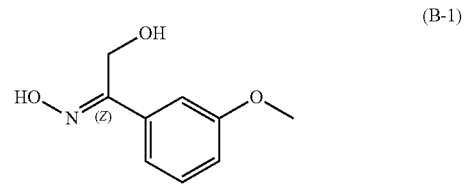
(B-1)

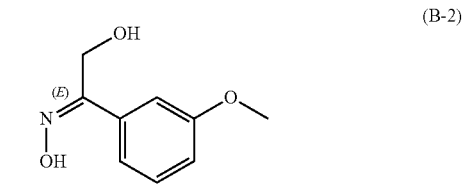
(B-2)

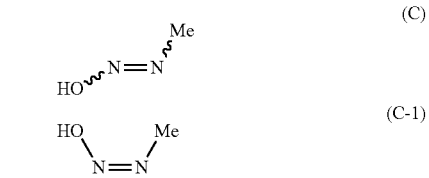
(C)

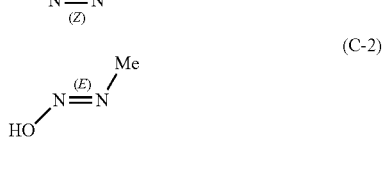
(C-1)

(C-2)

Unless otherwise specified, the terms "tautomer" or "tautomeric form" means that different functional groups are in dynamic equilibrium at room temperature and can be rapidly converted into each other. If tautomers are possible (as in solution), a chemical equilibrium of tautomers can be achieved. For example, proton tautomers (also known as prototropic tautomers) include interconversions by proton transfer, such as keto-enol isomerization and imine-enamine isomerization. Valence tautomers include interconversions by recombination of some bonding electrons. A specific example of keto-enol tautomerization is interconversion between two tautomers pentane-2,4-dione and 4-hydroxypent-3-en-2-one.

Unless otherwise specified, the term "enriched in one isomer", "isomer enriched", "enriched in one enantiomer" or "enantiomeric enriched" means that the content of one isomer or enantiomer is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the term "isomer excess" or "enantiomeric excess" means the difference between the relative percentages of two isomers or two enantiomers. For example, if one isomer or enantiomer is present in an amount of 90% and the other isomer or enantiomer is present in an amount of 10%, the isomer or enantiomeric excess (ee value) is 80%.

Optically active (R)- and (S)-isomer, or D and L isomer can be prepared using chiral synthesis or chiral reagents or other conventional techniques. If one kind of enantiomer of certain compound disclosed herein is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to afford the pure enantiomer. In addition, the enantiomer and the diastereoisomer are generally isolated through chromatography which uses a chiral stationary phase and optionally combines with a chemical derivative method (for example, carbamate generated from amine).

Compounds disclosed herein may contain an unnatural proportion of atomic isotopes at one or more of the atoms that make up the compounds. For example, a compound may be labeled with a radioisotope such as tritium ($^3H$), iodine-125 ($^{125}I$) or C-14($^{14}C$). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is oxo (i.e., =O), it means two hydrogen atoms are substituted.

Positions on an aromatic ring cannot be substituted by oxo. The term "optionally substituted" means an atom can be substituted by a substituent or not, unless otherwise specified, the species and number of the substituent may be arbitrary so long as being chemically achievable.

When any variable (such as R) occurs in the constitution or structure of the compound more than once, the definition of the variable at each occurrence is independent. Thus, for example, if a group is substituted by 0 to 2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of variables is a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When an enumerated substituent does not indicate through which atom it is linked to the substituted group, such substituent can be bonded through any of its atoms. For example, a pyridyl group as a substituent may be linked to the substituted group through any one of carbon atoms on the pyridine ring.

When an enumerated linking group does not indicate its linking direction, its linking direction is arbitrary. For example, when the linking group L in

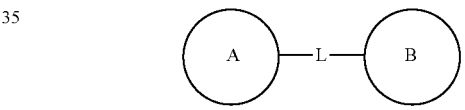

is -M-W—, the -M-W— can be linked to the ring A and the ring B in the same direction as the reading order from left to right to constitute

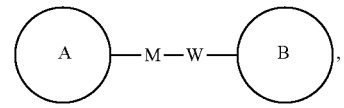, or can be linked to the ring A and the ring B in the reverse direction as the reading order from left to right to constitute

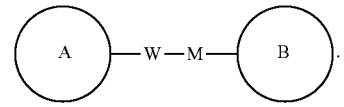.

A combination of the linking groups, substituents and/or variants thereof is allowed only when such combination can result in a stable compound.

Unless otherwise specified, when a group has one or more connectable sites, any one or more sites of the group can be connected to other groups through chemical bonds. The chemical bond between the site and other groups can be represented by a straight solid bond ( ⟋ ), a straight dashed bond ( ⁄ ), or a wavy line ( ⁄ ). For example, the straight solid bond in —OCH₃ indicates that the group is connected to other groups through the oxygen atom in the group; the straight dashed bond in

indicates that the group is connected to other groups through two ends of the nitrogen atom in the group; the wavy line in

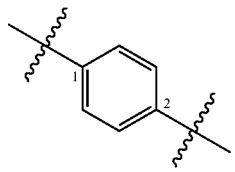 [SMILES: *c1ccc(*)cc1]

indicates that the group is connected to other groups through the 1- and 2-carbon atoms in the phenyl group.

Unless otherwise specified, the term "$C_{1-3}$ alkyl" is used to indicate a linear or branched saturated hydrocarbon group consisting of 1 to 3 carbon atoms. The $C_{1-3}$ alkyl group includes $C_{1-2}$ and $C_{2-3}$ alkyl groups and the like. It may be monovalent (e.g., methyl), divalent (e.g., methylene) or multivalent (e.g., methenyl). Examples of $C_{1-3}$ alkyl groups include, but are not limited to, methyl (Me), ethyl (Et), propyl (including n-propyl and isopropyl), and the like.

Unless otherwise specified, the term "$C_{1-3}$ alkoxy" refers to an alkyl group containing 1 to 3 carbon atoms and attached to the remainder of a molecule by an oxygen atom. The $C_{1-3}$ alkoxy group includes $C_{1-2}$, $C_{2-3}$, $C_3$ and $C_2$ alkoxy groups, and the like. Examples of $C_{1-3}$ alkoxy groups include, but are not limited to, methoxy, ethoxy, propoxy (including n-propoxy and isopropoxy), and the like.

Unless otherwise specified, the term "halo" or "halogen" by itself or as part of another substituent represents a fluorine, chlorine, bromine or iodine atom.

Unless otherwise specified, $C_{n-n+m}$ or $C_n-C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc.; similarly, n membered to n+m membered indicates that the number of atoms on a ring is n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, also includes any range from n to n+m, for example, 3-12 membered ring includes 3-6 membered ring, 3-9 membered ring, 5-6 membered ring, 5-7 membered ring, 6-7 membered ring, 6-8 membered ring, and 6-10 membered ring, and the like.

The term "leaving group" refers to a functional group or atom which can be replaced by another functional group or atom through a substitution reaction (such as nucleophilic substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g. acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

Compounds disclosed herein can be prepared by a variety of synthetic methods well known to those skilled in the art, including the following enumerated embodiment, the embodiment formed by the following enumerated embodiment in combination with other chemical synthesis methods, and equivalent replacement well known to those skilled in the art. Alternative embodiments include, but are not limited to the embodiment disclosed herein.

The structures of compounds disclosed herein can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Bruker D8 venture diffractometer with a light source of CuKα radiation in a scanning mode of φ/ω scan; after collecting the relevant data, the crystal structure is further analyzed by the direct method (Shelxs97) to confirm the absolute configuration.

Solvents used in the present disclosure are commercially available. The following abbreviation is used in the present disclosure: aq represents aqueous.

DETAILED DESCRIPTION OF THE INVENTION

Figure 1:
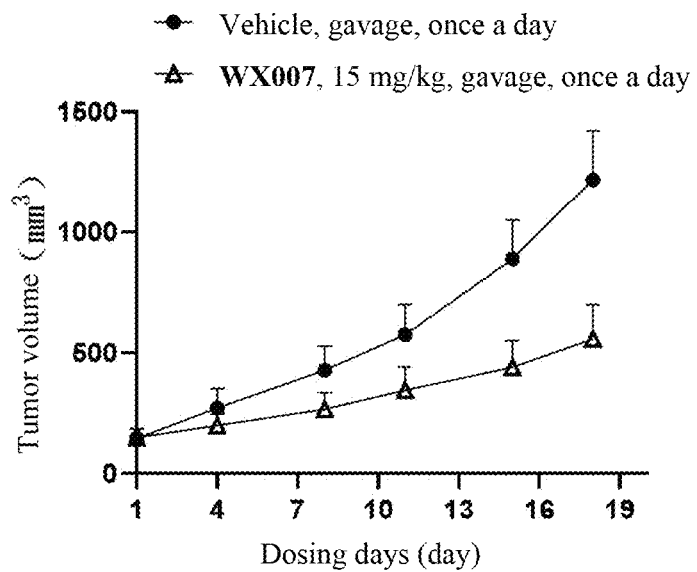
FIG. 1: Tumor growth curve of human colon cancer HCT116 in model animal after administration of solvent and WX007 respectively.

The present disclosure is described in detail below by means of examples. However, it is not intended that these examples have any disadvantageous limitations to the present disclosure. The present disclosure has been described in detail herein, and embodiments are also disclosed herein. It will be apparent to those skilled in the art that various changes and modifications may be made to the embodiments disclosed herein without departing from the spirit and scope disclosed herein.

Reference Example 1: Fragment A-1

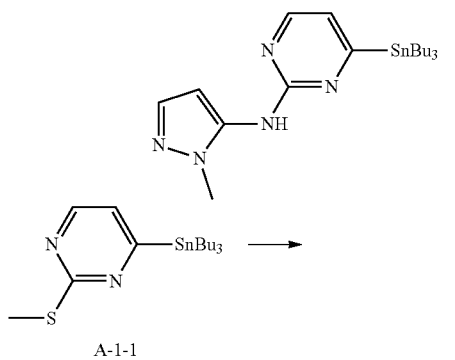

A-1-1

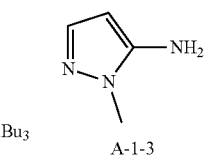

A-1-2

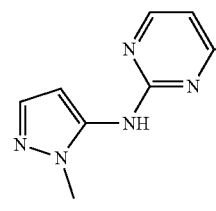

A-1

Step 1: Synthesis of Compound A-1-2

To a pre-dried single-necked flask was added a solution of sodium acetate (4.64 g, 56.60 mmol, 5 eq), potassium monopersulfate (13.92 g, 22.64 mmol, 2 eq) and water (47 mL). The mixture was cooled to 0° C. A solution of A-1-1 (4.7 g, 11.32 mmol, 1 eq), solvent tetrahydrofuran (47 mL) and methanol (47 mL) was added dropwise and the mixture was stirred at 0° C. for 1 hour. Then the mixture was stirred in an oil bath at 29° C. for 15 hours. After completion of the reaction, the reaction solution was poured into water (200 mL), and the aqueous phase was extracted with ethyl acetate (50 mL×3). The organic phases were combined, and the combined organic phase was sequentially washed with saturated brine (200 mL), dried over anhydrous sodium sulfate, and filtered. The filtrate was collected and concentrated under reduced pressure to give a residue. The residue was purified by flash column chromatography to give A-1-2. $^1$H NMR (400 MHz, CDCl$_3$) δ ppm 8.67 (d, J=4.9 Hz, 1H), 7.64 (d, J=4.9 Hz, 1H), 3.37 (s, 3H), 1.63-1.53 (m, 6H), 1.39-1.30 (m, 6H), 1.26-1.12 (m, 6H), 0.90 (t, J=7.3 Hz, 9H).

Step 2: Synthesis of Compound A-1

To a reaction flask were added A-1-2 (3.9 g, 8.72 mmol, 1 eq), A-1-3 (1.02 g, 10.46 mmol, 1.2 eq) and tetrahydrofuran (117 mL). The atmosphere was replaced with nitrogen gas, and then lithium hexamethyldisilazide (1 M, 18.31 mL, 2.1 eq) was added dropwise at −35° C. The mixture solution was reacted at −35° C. for 10 minutes. After completion of the reaction, the reaction solution was quenched with saturated aqueous ammonium chloride solution (100 mL), and extracted with ethyl acetate (100 mL×2) and dichloromethane (100 mL). The organic phase was dried over anhydrous sodium sulfate, and filtered. The filtrate was rotary evaporated to dryness to give a crude product. The crude product was purified by column chromatography to give A-1. $^1$H NMR (400 MHz, CDCl$_3$) δ ppm 8.17 (d, J=4.85 Hz, 1H), 7.46 (d, J=1.76 Hz, 1H), 6.91 (d, J=4.63 Hz, 1H), 6.60 (s, 1H), 6.32 (d, J=1.98 Hz, 1H), 3.79 (s, 3H), 1.52-1.61 (m, 6H), 1.28-1.40 (m, 6H), 1.03-1.20 (m, 6H), 0.89 (t, J=7.28 Hz, 9H).

Example 1

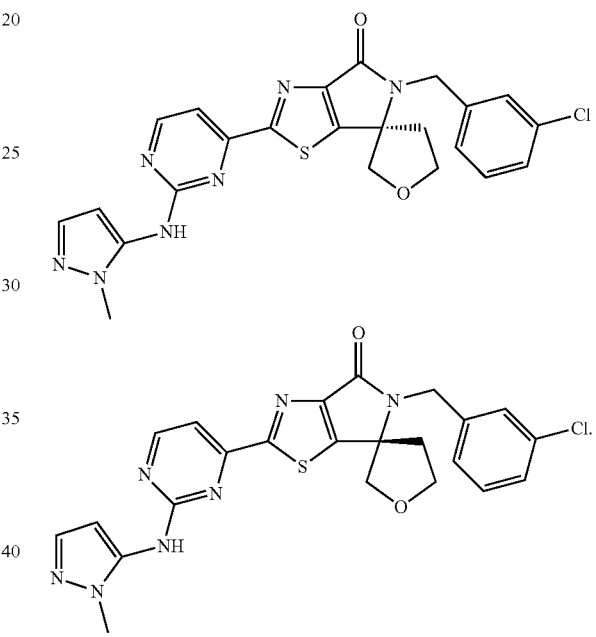

Route of Synthesis:

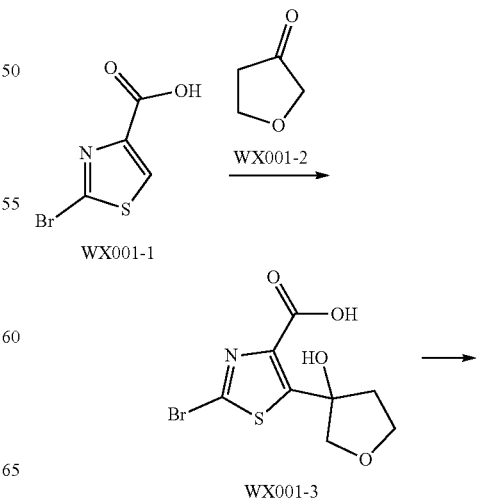

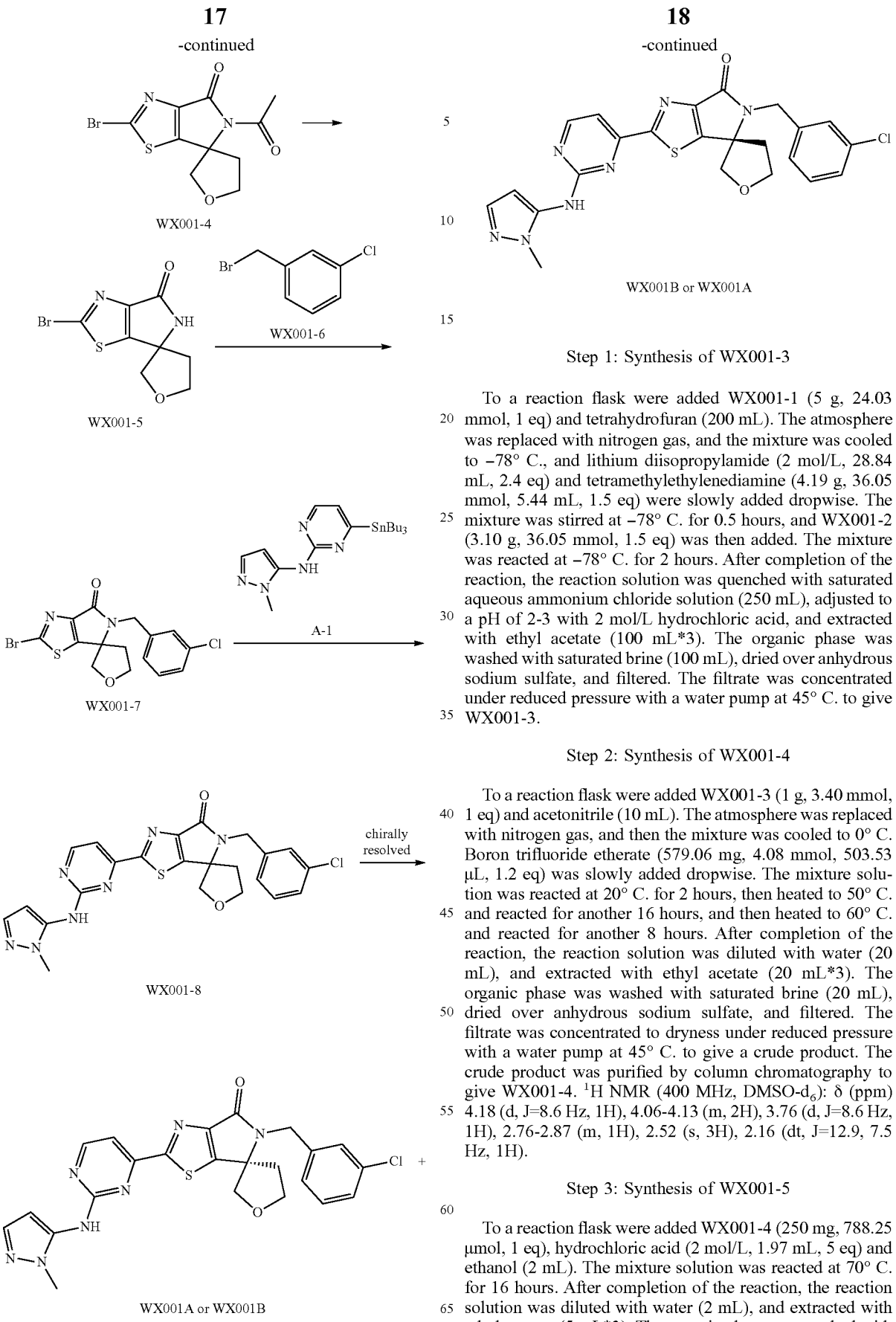

Step 1: Synthesis of WX001-3

To a reaction flask were added WX001-1 (5 g, 24.03 mmol, 1 eq) and tetrahydrofuran (200 mL). The atmosphere was replaced with nitrogen gas, and the mixture was cooled to −78° C., and lithium diisopropylamide (2 mol/L, 28.84 mL, 2.4 eq) and tetramethylethylenediamine (4.19 g, 36.05 mmol, 5.44 mL, 1.5 eq) were slowly added dropwise. The mixture was stirred at −78° C. for 0.5 hours, and WX001-2 (3.10 g, 36.05 mmol, 1.5 eq) was then added. The mixture was reacted at −78° C. for 2 hours. After completion of the reaction, the reaction solution was quenched with saturated aqueous ammonium chloride solution (250 mL), adjusted to a pH of 2-3 with 2 mol/L hydrochloric acid, and extracted with ethyl acetate (100 mL*3). The organic phase was washed with saturated brine (100 mL), dried over anhydrous sodium sulfate, and filtered. The filtrate was concentrated under reduced pressure with a water pump at 45° C. to give WX001-3.

Step 2: Synthesis of WX001-4

To a reaction flask were added WX001-3 (1 g, 3.40 mmol, 1 eq) and acetonitrile (10 mL). The atmosphere was replaced with nitrogen gas, and then the mixture was cooled to 0° C. Boron trifluoride etherate (579.06 mg, 4.08 mmol, 503.53 μL, 1.2 eq) was slowly added dropwise. The mixture solution was reacted at 20° C. for 2 hours, then heated to 50° C. and reacted for another 16 hours, and then heated to 60° C. and reacted for another 8 hours. After completion of the reaction, the reaction solution was diluted with water (20 mL), and extracted with ethyl acetate (20 mL*3). The organic phase was washed with saturated brine (20 mL), dried over anhydrous sodium sulfate, and filtered. The filtrate was concentrated to dryness under reduced pressure with a water pump at 45° C. to give a crude product. The crude product was purified by column chromatography to give WX001-4. $^1$H NMR (400 MHz, DMSO-$d_6$): δ (ppm) 4.18 (d, J=8.6 Hz, 1H), 4.06-4.13 (m, 2H), 3.76 (d, J=8.6 Hz, 1H), 2.76-2.87 (m, 1H), 2.52 (s, 3H), 2.16 (dt, J=12.9, 7.5 Hz, 1H).

Step 3: Synthesis of WX001-5

To a reaction flask were added WX001-4 (250 mg, 788.25 μmol, 1 eq), hydrochloric acid (2 mol/L, 1.97 mL, 5 eq) and ethanol (2 mL). The mixture solution was reacted at 70° C. for 16 hours. After completion of the reaction, the reaction solution was diluted with water (2 mL), and extracted with ethyl acetate (5 mL*3). The organic phase was washed with saturated brine (2 mL), dried over anhydrous sodium sulfate, and filtered. The filtrate was concentrated to dryness under reduced pressure with a water pump at 45° C. to give a crude product. The crude product was purified by thin layer chromatography on silica gel plate to give WX001-5. $^1$H NMR (400 MHz, DMSO-d$_6$): δ (ppm) 9.23 (br s, 1H), 3.97-4.14 (m, 2H), 3.84-3.95 (m, 1H), 3.76 (br d, J=8.7 Hz, 1H), 2.17-2.33 (m, 1H).

Step 4: Synthesis of WX001-7

To a reaction flask were added WX001-5 (150 mg, 545.21 μmol, 1 eq) and N,N-dimethylformamide (2 mL). The atmosphere was replaced with nitrogen gas, and then the mixture was cooled to 0° C. Sodium hydride (26.17 mg, 654.25 μmol, 60% purity, 1.2 eq) was added. The mixture was stirred for 0.5 hours, and WX001-6 (134.44 mg, 654.25 μmol, 85.63 μL, 1.2 eq) was then added. The mixture was slowly warmed to 20° C. and reacted for 0.5 hours. After completion of the reaction, the reaction solution was diluted with water (20 mL), and extracted with ethyl acetate (10 mL*3). The organic phase was washed with saturated brine (10 mL), dried over anhydrous sodium sulfate, and filtered. The filtrate was concentrated to dryness under reduced pressure with a water pump at 45° C. to give a crude product. The crude product was purified by thin layer chromatography on silica gel plate to give WX001-7. $^1$H NMR (400 MHz, DMSO-d$_6$): δ (ppm) 7.30-7.39 (m, 3H), 7.23-7.29 (m, 1H), 4.62-4.79 (m, 2H), 4.02-4.11 (m, 1H), 3.95 (q, J=8.4 Hz, 1H), 3.72-3.82 (m, 2H), 2.30-2.38 (m, 2H).

Step 5: Synthesis of WX001-8

To a reaction flask were added WX001-7 (100 mg, 250.19 μmol, 1 eq), A-1 (127.76 mg, 275.21 μmol, 1.1 eq) and toluene (2 mL). The atmosphere was replaced with nitrogen gas, and tetrakis(triphenylphosphine)palladium (57.82 mg, 50.04 μmol, 0.2 eq) was then added. The mixture solution was reacted at 125° C. for 14 hours. After completion of the reaction, the reaction solution was directly rotary evaporated to dryness to give a crude product. The crude product was purified by thin layer chromatography on silica gel plate to give WX001-8.

Step 6: Synthesis of WX001A or WX001B

WX001-8 was chirally resolved by supercritical fluid chromatography (separation condition: chromatographic column: DAICEL CHIRALCEL OJ (250*30 mm i.d. 10 μm); mobile phase: A was CO$_2$, B was ethanol (0.1% NH$_3$H$_2$O), B %=50%; flow rate: 70 mL/min) to give WX001A or WX001B. The retention time of WX001A was 1.782 minutes and the retention time of WX001B was 1.969 minutes.

Example 2

Route of Synthesis:

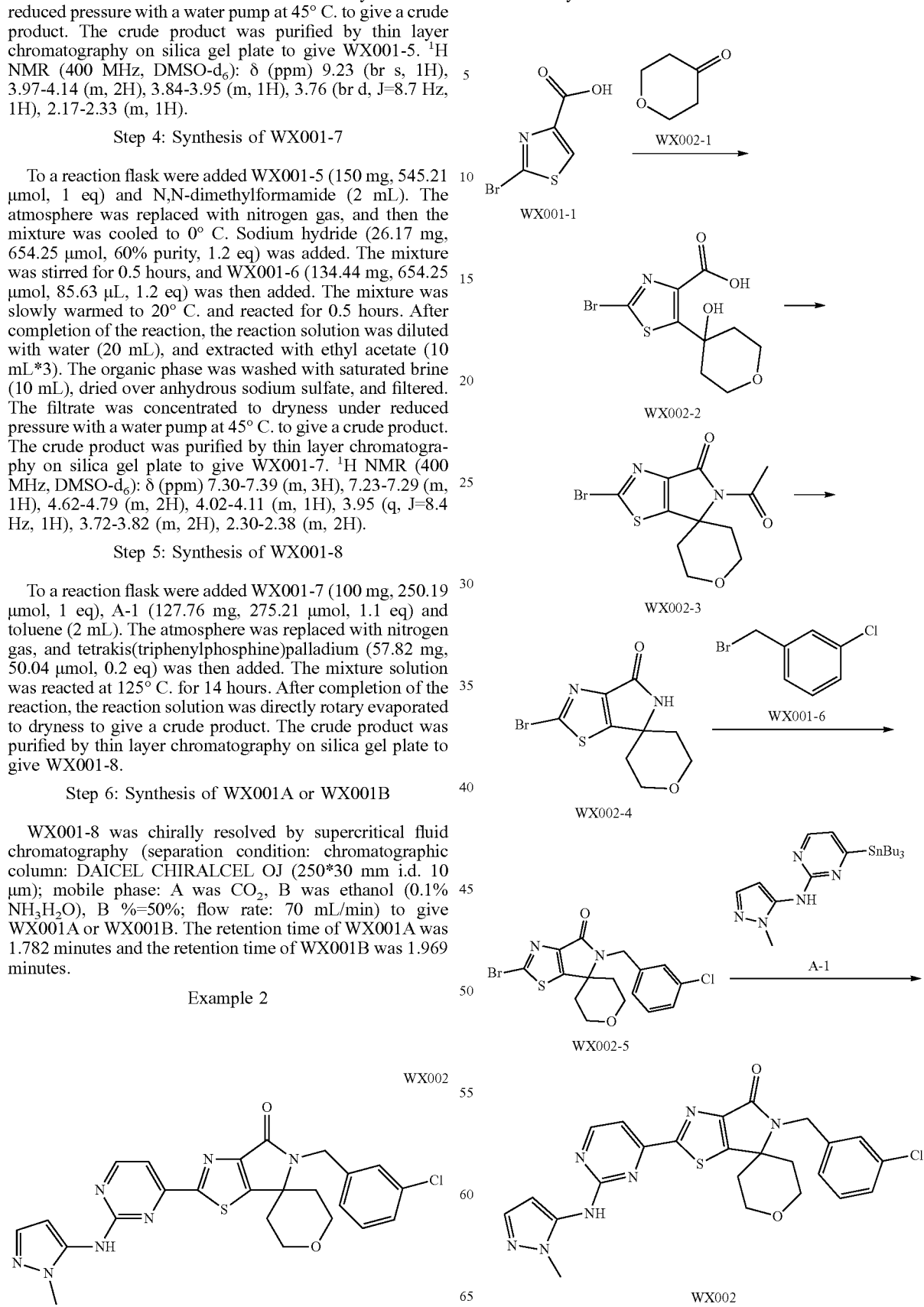

Step 1: Synthesis of WX002-2

To a reaction flask were added WX001-1 (5 g, 24.03 mmol, 1 eq) and tetrahydrofuran (250 mL) under nitrogen gas, and lithium diisopropylamide (2 M, 28.84 mL, 2.4 eq) and tetramethylethylenediamine (4.19 g, 36.05 mmol, 5.44 mL, 1.5 eq) were slowly added at −78° C. The mixture was reacted at −78° C. for 0.5 hours, and a solution of WX002-1 (4.81 g, 48.07 mmol, 4.42 mL, 2 eq) in tetrahydrofuran (10 mL) was then added. The mixture was reacted at −78° C. for 2 hours. After completion of the reaction, the reaction solution was slowly poured into 100 mL of saturated aqueous ammonium chloride solution at 0° C., adjusted to a pH of about 3-4 with hydrochloric acid (2 M), and extracted with ethyl acetate (200 mL*3). The organic phases were combined, washed with saturated brine (200 mL*3), dried over anhydrous sodium sulfate, and filtered. The filtrate was concentrated under reduced pressure with a water pump at 45° C. to give WX002-2.

Step 2: Synthesis of WX002-3

To a reaction flask were added WX002-2 (1 g, 3.25 mmol, 1 eq) and acetonitrile (20 mL). The atmosphere was replaced with nitrogen gas, and then boron trifluoride etherate (552.70 mg, 3.89 mmol, 480.61 µL, 1.2 eq) was added. The mixture solution was reacted at 60° C. for 16 hours. After completion of the reaction, saturated aqueous sodium bicarbonate solution (20 mL) was added to the reaction solution, and the mixture was extracted with ethyl acetate (30 mL*3). The organic phases were combined, washed with saturated brine (30 mL*3), dried over anhydrous sodium sulfate, and filtered. The filtrate was concentrated under reduced pressure with a water pump at 45° C. to give a crude product. The crude product was slurried with ethyl acetate (10 mL) to give WX002-3.

Step 3: Synthesis of WX002-4

To a dry reaction flask were added WX002-3 (260 mg, 785.06 µmol, 1 eq), hydrochloric acid (2 M, 4 mL, 10.19 eq) and ethanol (6 mL). The mixture was reacted at 50° C. for 16 hours, and then heated to 70° C. and reacted for 4 hours. After completion of the reaction, the reaction solution was extracted with ethyl acetate (50 mL*3). The organic phases were combined, washed with saturated brine (50 mL*3), dried over anhydrous sodium sulfate, and filtered. The filtrate was concentrated under reduced pressure with a water pump at 45° C. to give a crude product. The crude product was slurried with ethyl acetate (10 mL) to give WX002-4. $^1$H NMR (DMSO-$d_6$, 400 MHz): δ (ppm) 9.32 (s, 1H), 3.73-3.79 (m, 2H), 3.56-3.63 (m, 2H), 2.27-2.34 (m, 1H), 1.86-1.91 (m, 2H), 1.80-1.82 (m, 1H).

Step 4: Synthesis of WX002-5

To a dry reaction flask were added WX002-4 (50 mg, 172.92 µmol, 1 eq) and N,N-dimethylformamide (2 mL). The atmosphere was replaced with nitrogen gas, and then sodium hydride (10.37 mg, 259.38 µmol, 60% purity, 1.5 eq) was added at 0° C. The mixture was reacted at 0° C. for 0.5 hours, and WX001-6 (35.53 mg, 172.92 µmol, 22.63 µL, 1 eq) was then added. The reaction solution was slowly warmed to 25° C. and reacted for another 1.5 hours. After completion of the reaction, the reaction solution was added to 30 mL of water, and the mixture was extracted with ethyl acetate (50 mL*3). The organic phases were combined, washed with saturated brine (50 mL*3), dried over anhydrous sodium sulfate, and filtered. The filtrate was concentrated under reduced pressure with a water pump at 45° C. to give a crude product. The crude product was purified by thin layer chromatography on silica gel plate to give WX002-5. $^1$H NMR (DMSO-$d_6$, 400 MHz): δ (ppm) 7.42 (s, 1H), 7.29-7.38 (m, 3H), 4.77 (s, 2H), 4.03 (br dd, J=12.3, 4.1 Hz, 2H), 3.45 (br t, J=12.0 Hz, 2H), 2.17-2.25 (m, 4.8 Hz, 2H), 1.38 (br d, J=13.0 Hz, 2H).

Step 5: Synthesis of WX002

To a reaction flask were added WX002-5 (50 mg, 120.86 µmol, 1 eq), A-1 (65.66 mg, 120.86 µmol, 1 eq) and toluene (1 mL), and the atmosphere was replaced with nitrogen gas. The mixture was heated to 125° C., and tetrakis(triphenylphosphine)palladium (27.93 mg, 24.17 µmol, 0.2 eq) was then slowly added. The mixture was reacted at 125° C. for 48 hours. After completion of the reaction, the reaction solution was concentrated under reduced pressure with a water pump at 45° C. to give a crude product. The crude product was purified by high performance liquid chromatography (chromatographic column: Waters Xbridge BEH C18 100*30 mm*10 µm; mobile phase: [water (10 mM ammonium bicarbonate)-acetonitrile]; acetonitrile: 28%-58%, 8 min) to give WX002.

Example 3

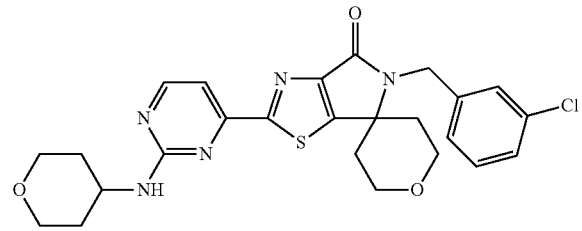

WX003

Route of Synthesis:

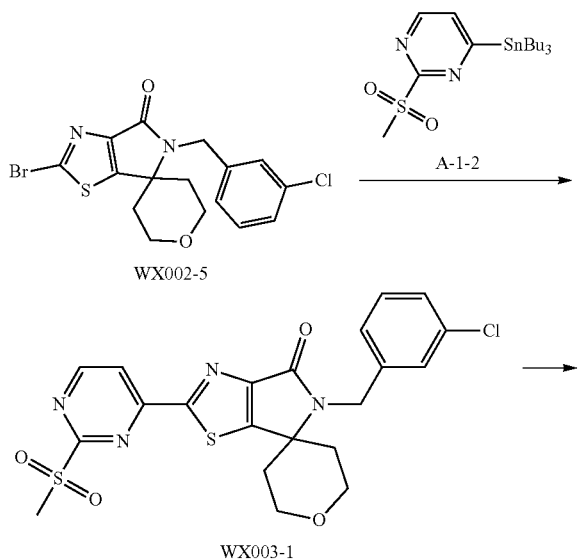

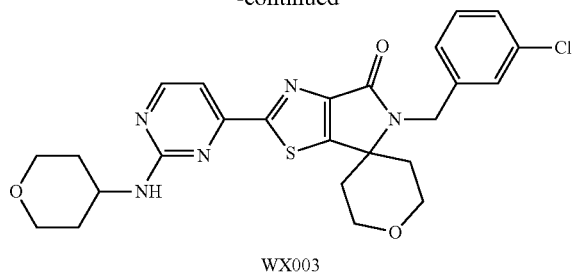

WX003

Step 1: Synthesis of WX003-1

To a pre-dried reaction flask were added WX002-5 (100 mg, 241.71 μmol, 1 eq), A-1-2 (108.10 mg, 241.71 μmol, 1 eq) and toluene (2 mL), and the atmosphere was replaced with nitrogen gas. Tetrakis(triphenylphosphine)palladium (55.86 mg, 48.34 μmol, 0.2 eq) was added at 125° C., and the mixture was reacted with stirring for 48 hours. After completion of the reaction, the reaction solution was concentrated under reduced pressure with a water pump at 45° C. to give a crude product. The crude product was purified by thin layer chromatography on silica gel plate to give WX003-1. $^1$H NMR (DMSO-$d_6$, 400 MHz): δ (ppm) 9.29 (d, J=5.1 Hz, 1H), 8.48 (d, J=5.1 Hz, 1H), 7.45 (s, 1H), 7.31-7.39 (m, 3H), 4.83 (s, 2H), 4.07 (m, J=12.3, 4.4 Hz, 2H), 3.64 (m, J=12.0 Hz, 2H), 3.54 (s, 3H), 2.24-2.31 (m, 2H), 1.43 (m, J=12.9 Hz, 2H).

Step 2: Synthesis of WX003

To a pre-dried reaction flask were added WX003-1 (50 mg, 101.84 μmol, 1 eq), tetrahydropyran-4-amine (10.30 mg, 101.84 μmol, 1 eq) and dimethyl sulfoxide (1 mL). The mixture was reacted with stirring at 100° C. for 16 hours. After completion of the reaction, the reaction solution was purified by high performance liquid chromatography (chromatographic column: Waters Xbridge BEH C18 100*30 mm*10 μm; mobile phase: [water (10 mM ammonium bicarbonate)-acetonitrile]; acetonitrile: 32%-62%, 8 min) to give WX003.

Example 4

WX004

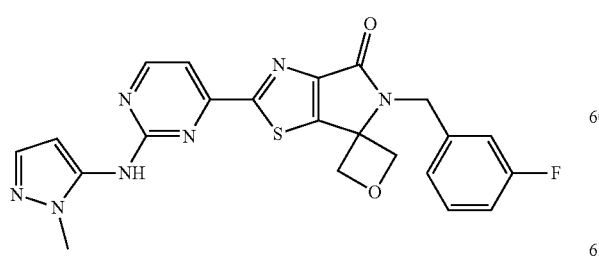

Route of Synthesis:

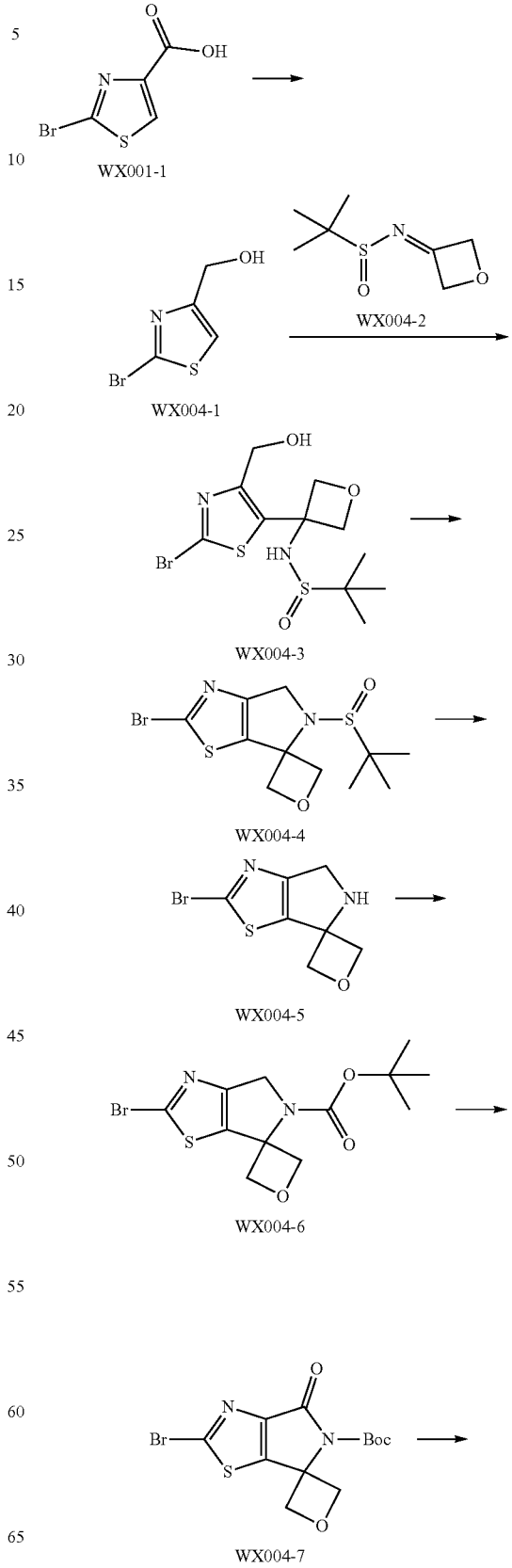

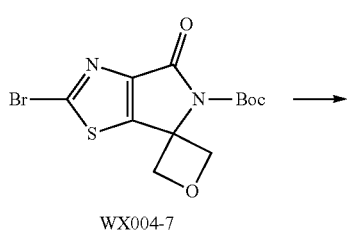

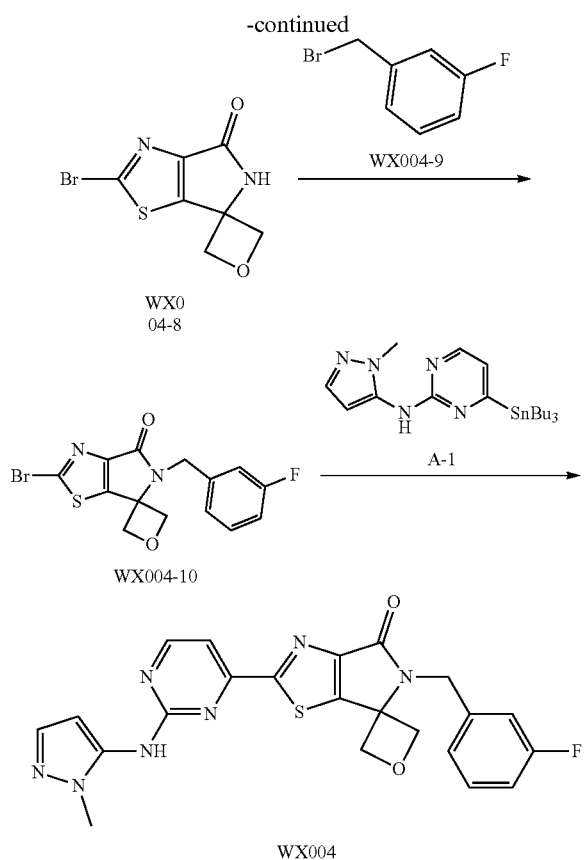

Step 1: Synthesis of WX004-1

To a reaction flask were added WX001-1 (10 g, 48.07 mmol, 1 eq) and tetrahydrofuran (200 mL). The atmosphere was replaced with nitrogen gas, and a solution of borane-tetrahydrofuran complex (1 M, 144.21 mL, 3 eq) was then slowly added dropwise under nitrogen gas. The mixture was reacted at 25° C. for 5 hours. After completion of the reaction, methanol (100 mL) was slowly added dropwise to the reaction solution under nitrogen gas. The mixture was stirred at 25° C. for 16 hours, and then rotary evaporated to dryness at 40° C. to give a crude product. The crude product was purified by column chromatography to give WX004-1. $^1$H NMR (CDCl$_3$, 400 MHz): δ (ppm) 7.47 (s, 1H), 4.52 (d, J=1.0 Hz, 2H).

Step 2: Synthesis of WX004-3

To a reaction flask were added WX004-1 (7.86 g, 40.51 mmol, 1 eq) and tetrahydrofuran (78.6 mL), and the atmosphere was replaced with nitrogen gas. The mixture was cooled to −78° C. Lithium diisopropylamide (2 M, 48.61 mL, 2.4 eq) was slowly added, and tetramethylethylenediamine (7.06 g, 60.76 mmol, 9.17 mL, 1.5 eq) was then added. The mixture was reacted at −78° C. for 0.5 hours, and a mixed solution of WX004-2 (10.65 g, 60.76 mmol, 1.5 eq) and tetrahydrofuran (10 mL) was then added. The mixture was reacted at −78° C. for 1 hour. After completion of the reaction, the reaction solution was quenched with saturated aqueous ammonium chloride solution (100 mL), and extracted with ethyl acetate (50 mL*3). The organic phase was dried over anhydrous sodium sulfate, and filtered. The filtrate was rotary evaporated to dryness at 45° C. to give a crude product. The crude product was purified by column chromatography to give WX004-3. $^1$H NMR (DMSO-d$_6$, 400 MHz): δ (ppm) 6.39 (s, 1H), 5.42 (t, J=5.6 Hz, 1H), 4.84-5.03 (m, 4H), 4.38 (d, J=5.6 Hz, 2H), 1.12 (s, 9H).

Step 3: Synthesis of WX004-4

To a reaction flask were added tetrahydrofuran (56 mL), WX004-3 (5.6 g, 11.07 mmol, 73% purity, 1 eq) and tributylphosphine (4.48 g, 22.14 mmol, 5.46 mL, 2 eq). After completion of the dissolution, the atmosphere was replaced with nitrogen gas. The mixture was cooled to 0° C., and diisopropyl azodicarboxylate (4.48 g, 22.14 mmol, 4.30 mL, 2 eq) was slowly added. The mixture was slowly warmed to 20° C. and reacted for 2 hours. After completion of the reaction, water (60 mL) was added to the reaction solution, and the mixture was extracted with ethyl acetate (30 mL*3). The organic phase was dried over anhydrous sodium sulfate, and filtered. The filtrate was rotary evaporated to dryness at 45° C. to give a crude product. The crude product was purified by column chromatography to give WX004-4. $^1$H NMR (DMSO-d$_6$, 400 MHz): δ (ppm) 5.30 (d, J=7.6 Hz, 1H), 4.75-4.87 (m, 3H), 4.61 (d, J=12.8 Hz, 1H), 4.22 (d, J=12.8 Hz, 1H), 1.27 (s, 9H).

Step 4: Synthesis of WX004-5

To a reaction flask were added WX004-4 (500 mg, 1.42 mmol, 1 eq), tetrahydrofuran (8.3 mL), water (1.6 mL) and iodine (72.25 mg, 284.67 μmol, 57.34 μL, 0.2 eq). The atmosphere was replaced with nitrogen gas, and the mixture was reacted at 30° C. for 16 hours. After completion of the reaction, the reaction solution containing WX004-5 was obtained and directly used in the next reaction.

Step 5: Synthesis of WX004-6

To the reaction solution containing WX004-5 obtained in Step 4 were sequentially added tetrahydrofuran (8.3 mL), water (1.6 mL), di-tert-butyl dicarbonate (465.00 mg, 2.13 mmol, 489.47 μL, 1.5 eq) and sodium carbonate (301.10 mg, 2.84 mmol, 2 eq), and the mixture was reacted at 25° C. for 4 hours. After completion of the reaction, the reaction solution was quenched with water (10 mL), and extracted with ethyl acetate (5 mL*3). The organic phase was dried over anhydrous sodium sulfate, and filtered. The filtrate was rotary evaporated to dryness at 45° C. to give a crude product. The crude product was purified by column chromatography to give WX004-6. $^1$H NMR (DMSO-d$_6$, 400 MHz): δ (ppm) 5.46 (br d, J=5.8 Hz, 1H), 5.32 (br d, J=6.3 Hz, 1H), 4.64 (br d, J=6.3 Hz, 1H), 4.55 (br d, J=5.8 Hz, 1H), 4.49 (br d, J=9.5 Hz, 2H), 1.47-1.57 (m, 9H).

Step 6: Synthesis of WX004-7

To a dry reaction flask were added WX004-6 (150 mg, 431.99 μmol, 1 eq), chromium trioxide (86.39 mg, 863.99 μmol, 32.00 μL, 2 eq) and acetic acid (3 mL), and the mixture was reacted at 25° C. for 12 hours. After completion of the reaction, the reaction solution was diluted with water (3 mL), and extracted three times with dichloromethane (5 mL). The organic phases were combined, washed with saturated brine (5 mL), dried over anhydrous sodium sulfate, and filtered. The filtrate was concentrated under reduced pressure with a water pump to give a crude product. The crude product was purified by column chromatography to give WX004-7.

Step 7: Synthesis of WX004-8

To a dry reaction flask were added WX004-7 (70 mg, 193.79 μmol, 1 eq), dichloromethane (1 mL) and trifluoroacetic acid (287.47 mg, 2.52 mmol, 186.67 μL, 13.01 eq), and the mixture was reacted at 25° C. for 1 hour. After completion of the reaction, the reaction solution was directly concentrated to give a crude product, and the crude product was purified by thin layer chromatography on silica gel plate to give WX004-8. $^1$H NMR (DMSO-d$_6$, 400 MHz): δ (ppm) 9.59 (br, s, 1H), 4.89 (s, 4H).

Step 8: Synthesis of WX004-10

To a dry reaction flask were added WX004-8 (45 mg, 172.35 μmol, 1 eq), N,N-dimethylformamide (2 mL), cesium carbonate (84.23 mg, 258.53 μmol, 1.5 eq) and WX004-9 (39.09 mg, 206.82 μmol, 25.39 μL, 1.2 eq). The atmosphere was replaced with nitrogen gas, and the mixture was reacted at 25° C. for 12 hours. After completion of the reaction, the reaction solution was diluted with water (2 mL), and extracted three times with dichloromethane (2 mL). The organic phases were combined, washed with saturated brine (20 mL), dried over anhydrous sodium sulfate, and filtered. The filtrate was concentrated under reduced pressure with a water pump to give a crude product, and the crude product was purified by thin layer chromatography on silica gel plate to give WX004-10.

Step 9: Synthesis of WX004-10

To a dry reaction flask were added WX004-10 (45 mg, 121.88 μmol, 1 eq), A-1 (62.24 mg, 134.07 μmol, 1.1 eq) and toluene (1 mL). The atmosphere was replaced with nitrogen gas, and tetrakis(triphenylphosphine)palladium (28.17 mg, 24.38 μmol, 0.2 eq) was then added. The mixture was heated to 125° C. and reacted for 16 hours. After completion of the reaction, the reaction solution was directly concentrated to give a crude product. The crude product was purified by thin layer chromatography on silica gel plate, and then purified by high performance liquid chromatography (chromatographic column: Waters Xbridge BEH C18 100*30 mm*10 μm; mobile phase: [H$_2$O (10 mM ammonium bicarbonate)-acetonitrile]; acetonitrile %: 25%-45%, 8 min) to give WX004.

Example 5

WX005

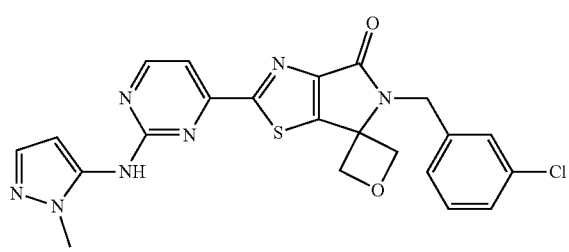

Route of Synthesis:

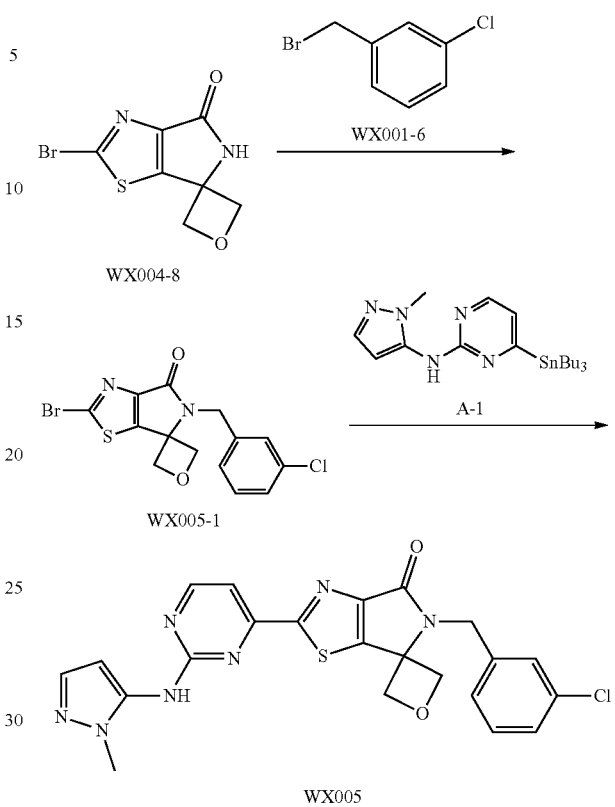

Step 1: Synthesis of WX005-1

To a dry reaction flask were added WX004-8 (300 mg, 1.15 mmol, 1 eq), N,N-dimethylformamide (6 mL), cesium carbonate (561.55 mg, 1.72 mmol, 1.5 eq) and WX001-6 (283.32 mg, 1.38 mmol, 180.46 μL, 1.2 eq). The atmosphere was replaced with nitrogen gas, and the mixture was reacted at 25° C. for 16 hours. After completion of the reaction, the reaction solution was diluted with water (10 mL), and extracted three times with ethyl acetate (20 mL). The organic phases were combined, washed with saturated brine (20 mL*5), dried over anhydrous sodium sulfate, and filtered. The filtrate was concentrated under reduced pressure with a water pump to give a crude product. The crude product was purified by column chromatography to give WX005-1. $^1$H NMR (DMSO-d6, 400 MHz): δ (ppm) 7.42 (s, 1H), 7.32-7.40 (m, 2H), 7.26-7.32 (m, 1H), 4.98 (s, 2H), 4.79-4.89 (m, 4H)

Step 2: Synthesis of WX005

To a dry reaction flask were added WX005-1 (30 mg, 77.79 μmol, 1 eq), A-1 (39.72 mg, 85.57 μmol, 1.1 eq) and toluene (1 mL). The atmosphere was replaced with nitrogen gas, and tetrakis(triphenylphosphine)palladium (17.98 mg, 15.56 μmol, 0.2 eq) was then added. The mixture was heated to 125° C. and reacted for 16 hours. Additional tetrakis (triphenylphosphine)palladium (8.99 mg, 7.78 μmol, 0.1 eq) was added, and the mixture was reacted at 125° C. for 3 hours. After completion of the reaction, the reaction solution was directly concentrated to give a crude product. The crude product was purified by thin layer chromatography on silica gel plate, and then purified by high performance liquid chromatography (chromatographic column: Waters Xbridge BEH C18 100*30 mm*10 μm; mobile phase: [water (10 mM ammonium bicarbonate)-acetonitrile]; acetonitrile %: 25%-55%, 8 min) to give WX005.

Example 6

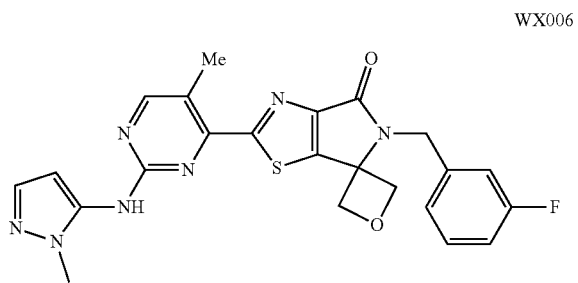 [SMILES: Cc1cnc(Nc2ccnn2C)nc1-c1nc2c(s1)C1(COC1)N(Cc1cccc(F)c1)C2=O]

WX006

Route of Synthesis:

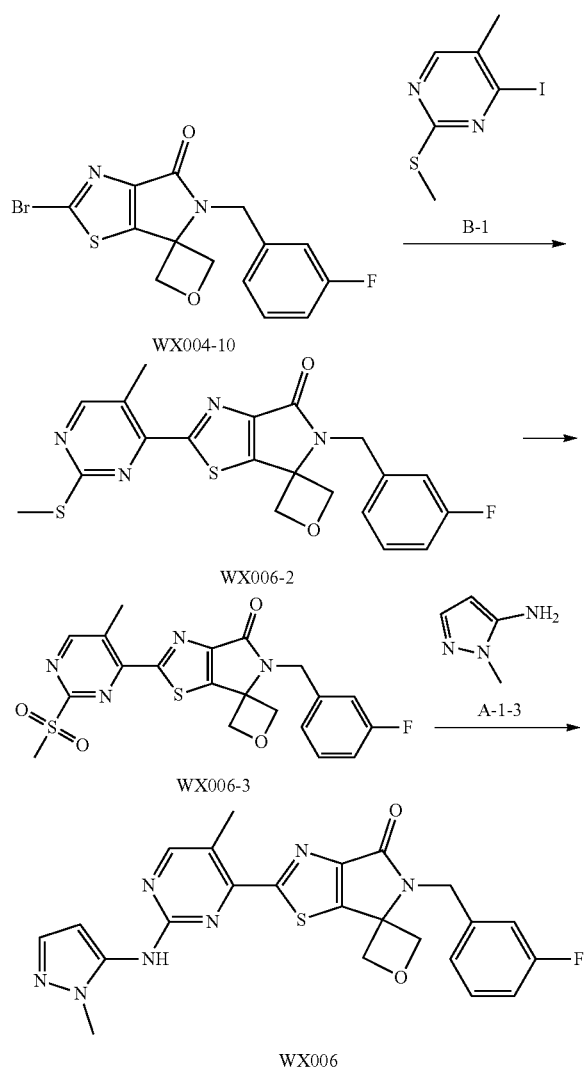

Step 1: Synthesis of WX006-2

To a dry reaction flask were added WX004-10 (105 mg, 284.39 μmol, 1 eq), tetrahydrofuran (1 mL) and zinc chloride (0.7 M, 406.27 μL, 1 eq). The atmosphere was replaced with nitrogen gas, and n-butyl lithium (2.5 M, 170.64 μL, 1.5 eq) was added at −30° C. The mixture was stirred at 25° C. for 1 hour, and then cooled to −30° C. A solution of B-1 (75.68 mg, 284.39 μmol, 1 eq) and tetrakis(triphenylphosphine)palladium (16.43 mg, 14.22 μmol, 0.05 eq) in tetrahydrofuran (0.5 mL) was added, and the mixture was heated to 60° C. and reacted for another 16 hours. After completion of the reaction, 2 mL of saturated aqueous ammonium chloride solution was added to the reaction solution, and the mixture was extracted with ethyl acetate (5 mL*3). The organic phases were combined, washed with saturated brine (20 mL), dried over anhydrous sodium sulfate, and filtered. The filtrate was concentrated under reduced pressure with a water pump to give a crude product. The crude product was purified by slurrying with 2 mL of methyl tert-butyl ether to give WX006-2. $^1$H NMR (DMSO-$d_6$, 400 MHz): δ (ppm) 8.77 (s, 1H), 7.37-7.42 (m, 1H), 7.20 (br d, J=8.6 Hz, 3H), 5.04 (s, 2H), 4.94 (d, J=7.5 Hz, 2H), 4.86 (d, J=7.2 Hz, 2H), 2.64 (s, 3H), 2.62 (s, 3H).

Step 2: Synthesis of WX006-3

To a dry reaction flask were added WX006-2 (20 mg, 46.67 μmol, 1 eq) and dichloromethane (1 mL). The atmosphere was replaced with nitrogen gas, and then m-chloroperoxybenzoic acid (30.20 mg, 140.02 μmol, 80% purity, 3 eq) was added at 0° C. The mixture was slowly warmed to 25° C. and reacted for 3 hours. After completion of the reaction, saturated sodium thiosulfate solution (10 mL) was added to the reaction solution until the color of starch potassium iodide test paper was not changed to blue. The mixture was diluted with dichloromethane (10 mL). The layers were separated. The organic phase was then collected, and the collected organic phase was washed respectively with 10 mL of saturated sodium bicarbonate solution and 10 mL of saturated brine, dried over anhydrous sodium sulfate, and filtered. The filtrate was rotary evaporated to dryness to give a crude product. The crude product was purified by thin layer chromatography on silica gel plate to give WX006-3. $^1$H NMR (DMSO-$d_6$, 400 MHz): δ (ppm) 9.20 (s, 1H), 7.37-7.45 (m, 1H), 7.21 (br d, J=8.0 Hz, 2H), 7.09-7.15 (m, 1H), 5.05 (s, 2H), 4.93-4.96 (m, 2H), 4.89-4.91 (m, 2H), 3.51 (s, 3H), 2.82 (s, 3H).

Step 3: Synthesis of WX006

To a dry reaction flask were added WX006-3 (28 mg, 60.80 μmol, 1 eq), A-1-3 (11.81 mg, 121.61 μmol, 2 eq), dichloromethane (1 mL) and tetrahydrofuran (1 mL). The atmosphere was replaced with nitrogen gas, and lithium hexamethyldisilazide (1 M, 127.69 μL, 2.1 eq) was added at −30° C. The mixture was reacted at 25° C. for 1 hour. After completion of the reaction, 1 mL of water was added to the reaction solution. The organic solvent in the reaction solution was rotary evaporated, and solids were precipitated. The mixture was filtered, and the solids were collected to give a crude product. The crude product was purified by high performance liquid chromatography (chromatographic column: Waters Xbridge BEH C18 100*25 mm*5 μm; mobile phase: [$H_2O$ (10 mM ammonium bicarbonate)-acetonitrile]; acetonitrile %: 25%-60%, 10 min) to give WX006.

Example 7

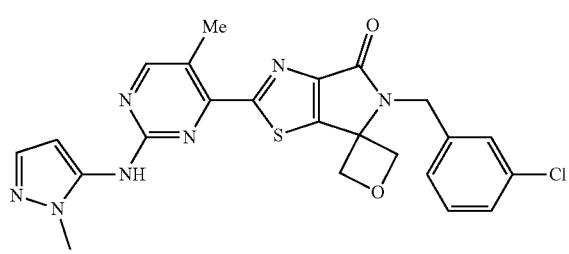

Route of Synthesis:

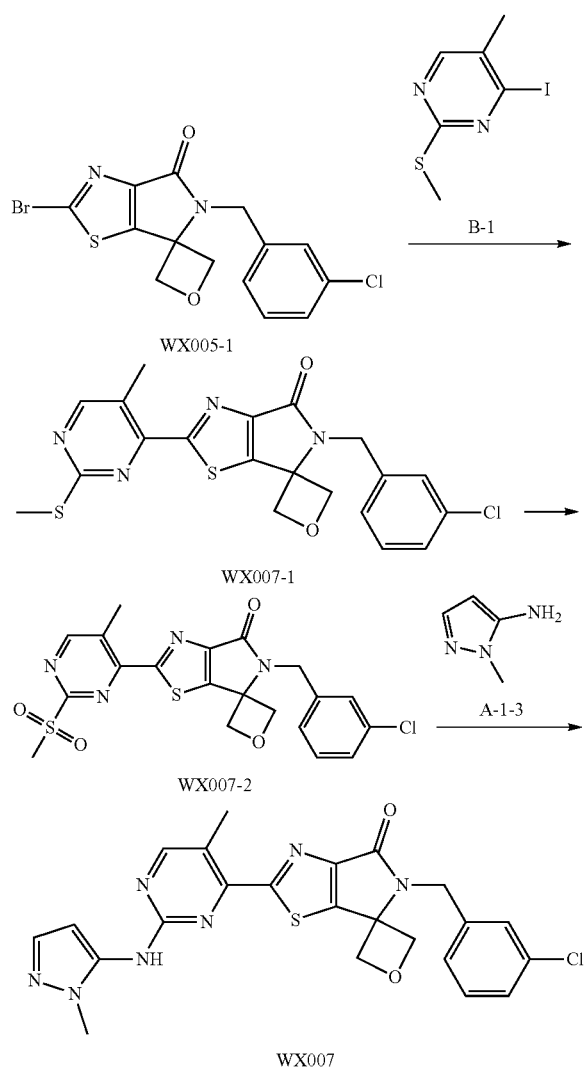

Step 1: Synthesis of WX007-1

To a dry reaction flask were added WX005-1 (100 mg, 259.29 μmol, 1 eq), zinc chloride (0.7 M, 370.42 μL, 1 eq) and tetrahydrofuran (1.5 mL). The atmosphere was replaced with nitrogen gas, and then the mixture was cooled to −30° C. n-Butyl lithium (2.5 M, 155.58 μL, 1.5 eq) was added, and the mixture was reacted at 20° C. for 1 hour. The mixture was then cooled to −30° C. A solution of tetrakis(triphenylphosphine)palladium (14.98 mg, 12.96 μmol, 0.05 eq) and B-1 (69.00 mg, 259.29 μmol, 1 eq) in tetrahydrofuran (0.5 mL) was slowly added dropwise, and the mixture was reacted at 60° C. for 15 hours. After completion of the reaction, the reaction solution was quenched with 5 mL of saturated ammonium chloride solution, and extracted three times with ethyl acetate (10 mL). The organic phases were combined, washed with saturated brine (10 mL), dried over anhydrous sodium sulfate, and filtered. The filtrate was concentrated under reduced pressure with a water pump to give a crude product. The crude product was purified by thin layer chromatography on silica gel plate to give WX007-1.
$^1$H NMR (DMSO-$d_6$, 400 MHz): δ (ppm) 8.78 (s, 1H), 7.45 (s, 1H), 7.30-7.42 (m, 3H), 5.03 (s, 2H), 4.91-4.96 (m, 2H), 4.83-4.89 (m, 2H), 2.59-2.71 (m, 6H).

Step 2: Synthesis of WX007-2

To a dry reaction flask were added WX007-1 (40 mg, 89.90 μmol, 1 eq) and dichloromethane (1 mL). The atmosphere was replaced with nitrogen gas, and then m-chloroperoxybenzoic acid (58.18 mg, 269.69 μmol, 80% purity, 3 eq) was added at 0° C. The mixture was slowly warmed to 25° C. and reacted for 3 hours. After completion of the reaction, saturated sodium thiosulfate solution (10 mL) was added to the reaction solution until the color of starch KI test paper was not changed to blue. The mixture solution was diluted with dichloromethane (10 mL). The layers were separated. The organic phase was then collected, and the collected organic phase was respectively washed with 10 mL of saturated sodium bicarbonate solution and 10 mL of saturated brine, dried over anhydrous sodium sulfate, and filtered. The filtrate was rotary evaporated to dryness to give a crude product. The crude product was purified by thin layer chromatography on silica gel plate to give WX007-2.

Step 3: Synthesis of WX007

To a dry reaction flask were added WX007-2 (35 mg, 73.38 μmol, 1 eq), A-1-3 (14.97 mg, 154.10 μmol, 2.1 eq), dichloromethane (0.5 mL) and tetrahydrofuran (0.5 mL). The atmosphere was replaced with nitrogen gas. The mixture was cooled to 0° C., and lithium hexamethyldisilazide (1 M, 146.76 μL, 2 eq) was added dropwise. The mixture was reacted at 0° C. for 0.5 hours and reacted at 25° C. for another 1 hour. After completion of the reaction, the reaction solution was quenched with 10 mL of water, and extracted with 20 mL of dichloromethane. The layers were separated. The organic phase was collected, and the aqueous phase was extracted with dichloromethane (3*20 mL). The organic phases were combined, and the combined organic phase was sequentially washed with saturated brine (3*20 mL), dried over anhydrous sodium sulfate, and concentrated under reduced pressure to give a residue. The crude product was purified by high performance liquid chromatography (chromatographic column: Phenomenex Gemini-NX C18 75*30 mm*3 μm; mobile phase: [$H_2O$ (10 mM ammonium bicarbonate)-acetonitrile]; acetonitrile %: 35%-55%, 8 min) to give WX007.

The data of $^1$H NMR spectrum and mass spectrum of each example were shown in Table 1.

TABLE 1

| Example | Compound | NMR | MS m/z |
|---|---|---|---|
| 1 | WX001A | $^1$H NMR (400 MHz, DMSO-$d_6$): δ (ppm) 9.81 (br s, 1H), 8.70 (d, J = 4.9 Hz, 1H), 7.55 (d, J = 5.0 Hz, 1H), 7.25-7.45 (m, 5H), 6.32 (s, 1H), 4.67-4.83 (m, 2H), 3.99-4.13 (m, 2H), 3.82-3.88 (m, 1H), 3.76-3.81 (m, 1H), 3.72 (s, 3H), 2.35-2.45 (m, 2H). | 494.2 [M + H]$^+$ |
|  | WX001B | $^1$H NMR (400 MHz, DMSO-$d_6$): δ (ppm) 9.80 (br s, 1H), 8.69 (d, J = 4.9 Hz, 1H), 7.55 (d, J = 4.9 Hz, 1H), 7.25-7.46 (m, 5H), 6.32 (d, J = 1.6 Hz, 1H), 4.67-4.84 (m, 2H), 3.98-4.14 (m, 2H), 3.83-3.88 (m, 1H), 3.76-3.81 (m, 1H), 3.72 (s, 3H), 2.33-2.45 (m, 2H). | 494.1 [M + H]$^+$ |
| 2 | WX002 | $^1$H NMR (DMSO-$d_6$, 400 MHz): δ (ppm) 9.81 (s, 1H), 8.71 (d, J = 4.9 Hz, 1H), 7.58 (d, J = 5.0 Hz, 1H), 7.44 (s, 1H), 7.42 (d, J = 1.9 Hz, 1H), 7.30-7.40 (m, 3H), 6.34 (d, J = 1.5 Hz, 1H), 4.81 (s, 2H), 4.07 (br dd, J = 12.1, 4.0 Hz, 2H), 3.74 (s, 3H), 3.57 (br t, J = 12.0 Hz, 2H), 2.23-2.31 (m 4.5 Hz, 2H), 1.40 (br d, J = 12.7 Hz, 2H). | 508.3 [M + 1]$^+$ |
| 3 | WX003 | $^1$H NMR (DMSO-$d_6$, 400 MHz): δ (ppm) 8.54 (br d, J = 5.0 Hz, 1H), 7.51-7.69 (m, 1H), 7.44 (s, 1H), 7.30-7.39 (m, 3H), 7.28 (d, J = 4.9 Hz, 1H), 4.80 (s, 2H), 4.06 (br dd, J = 12.9, 3.9 Hz, 3H), 3.90 (br d, J = 11.0 Hz, 2H), 3.53-3.64 (m, 2H), 3.37-3.51 (m, 2H), 2.22-2.29 (m, 4.6 Hz, 2H), 1.82-1.94 (m, 2H), 1.51-1.63 (m, 2H), 1.40 (br d, J = 12.7 Hz, 2H). | 512.3 [M + 1]$^+$ |
| 4 | WX004 | $^1$H NMR (DMSO-$d_6$, 400 MHz): δ (ppm) 9.84 (br s, 1H), 8.70 (d, J = 5.1 Hz, 1H), 7.55 (d, J = 4.9 Hz, 1H), 7.36-7.44 (m, 2H), 7.15-7.21 (m, 2H), 7.06-7.15 (m, 1H), 6.35 (s, 1H), 5.03 (s, 2H), 4.89-4.95 (m, 2H), 4.83-4.88 (m, 2H), 3.74 (s, 3H). | 464.0 [M + 1]$^+$ |
| 5 | WX005 | $^1$H NMR (DMSO-$d_6$, 400 MHz): δ(ppm) 9.84 (br s, 1H), 8.71 (d, J = 4.9 Hz, 1H), 7.55 (d, J = 5.0 Hz, 1H), 7.29-7.46 (m, 5H), 6.35 (d, J = 1.5 Hz, 1H), 5.02 (s, 2H), 4.89-4.94 (m, 2H), 4.84-4.89 (m, 2H), 3.74 (s, 3H). | 480.1 [M + 1]$^+$ |
| 6 | WX006 | $^1$H NMR (DMSO-$d_6$, 400 MHz): δ (ppm) 9.68 (s, 1H), 8.62 (s, 1H), 7.37-7.43 (m, 2H), 7.16-7.21 (m, 2H), 7.08-7.15 (m, 1H), 6.36 (d, J = 1.8 Hz, 1H), 5.03 (s, 2H), 4.94 (d, J = 7.5 Hz, 2H), 4.83 (d, J = 7.3 Hz, 2H), 3.73 (s, 3H), 2.58 (s, 3H). | 478.1 [M + 1]$^+$ |
| 7 | WX007 | $^1$H NMR (DMSO-$d_6$, 400 MHz): δ(ppm) 9.66 (s, 1H), 8.62 (s, 1H), 7.28-7.46 (m, 5H), 6.36 (s, 1H), 5.02 (s, 2H), 4.94 (d, J = 7.3 Hz, 2H), 4.83 (d, J = 7.3 Hz, 2H), 3.73 (s, 3H), 2.59 (s, 3H). | 494.1 [M + 1]$^+$ |

Assay Example 1. Assay of In Vitro Kinase Activity

1. Purpose of the Assay:
The ability of compounds to inhibit ERK2 kinase activity was measured.

2. Assay Buffer:
20 mM Hepes (pH 7.5), 10 mM MgCl$_2$, 1 mM ethylenebis(oxyethylenenitrilo)tetraacetic acid (EGTA), 0.02% Brij35, 0.02 mg/mL bovine serum albumin (BSA), 0.1 mM Na$_3$VO$_4$, 2 mM dithiothreitol (DTT), 1% DMSO.

3. Processing of Compound:
The assay compound was dissolved in 100% DMSO to prepare a stock solution of specific concentration. The compound was serially diluted in DMSO solution using Integra Viaflo Assist smart pipette.

4. Method of the Assay
1) The substrate MBP was prepared in freshly prepared reaction buffer;
2) ERK2 kinase was added to the above-mentioned MBP solution and mixed gently;
3) The compound dissolved in 100% DMSO was added to the kinase reaction system using ultrasound technology (Echo550; nanoliter range), and the mixture was incubated at room temperature for 20 minutes;
4) $^{33}$P-ATP (specific concentration of 10 μCi/μL) was added to the reaction system, and the reaction was started at this time;
5) The mixture was incubated at room temperature for 2 hours;
6) The amount of radioactivity was detected by filter-binding method;
7) ERK2 kinase activity was calculated as the ratio of the remaining kinase activity in the assay sample to the kinase activity of the control group (treated by DMSO). Curve was fitted using Prism (GraphPad software) and IC$_{50}$ values were calculated.

5. The Assay Results were Shown in Table 2:

TABLE 2

Results of kinase activity assay in vitro

| Compound | ERK2 IC$_{50}$ (nM) |
|---|---|
| WX001A | 0.31 |
| WX001B | 0.32 |
| WX002 | 0.4 |
| WX003 | 0.29 |
| WX004 | 1.1 |
| WX005 | 0.36 |
| WX006 | 0.94 |
| WX007 | 0.48 |

Conclusion: The compounds of the present disclosure exhibit excellent activity of inhibiting ERK2 kinase.

Assay Example 2. In Vitro Cell Proliferation
Inhibition Assay

1. Purpose of the Assay:

The ability of compounds to inhibit the proliferation of HT29 tumor cells was measured.

2. Processing of Compound:

The assay compound was dissolved in 100% DMSO to prepare 10 mM stock solution.

3. Method and Step of the Assay

1) UV light of a biological safety cabin was turned on, and 30 minutes were counted down;

2) In a 37° C. water bath, RPMI1640 medium and trypsin were preheated;

3) After completion of the UV irradiation, the biological safety cabin was opened. The preheated medium, trypsin and phosphate buffered saline (PBS), etc. were wiped with alcohol and placed in the biological safety cabin;

4) HT29 cells were removed from the incubator, and the old medium was removed in biological safety cabin. 10 ml of PBS was added. The mixture was shaken gently, and then PBS was removed;

5) 1.5 ml of preheated 0.25% trypsin was added. The culture vessel was shaken horizontally so that the trypsin evenly covered the cells at the bottom, and placed in an incubator for 2 minutes;

6) Cell digestion was stopped with complete medium, and the cell suspension was pipetted to homogeneity and counted;

7) According to the result of cell counting, the density of cell suspension was adjusted to 1500 cells per well, and the cell suspension was seeded at 50 μl per well;

8) The stock solution of compounds was serially diluted in DMSO solution, and compounds were added to cell plate using Tecan;

9) The compound-added cell plate and CellTiterGlo were equilibrated at room temperature, and 25 microliters of CellTiterGlo was then added to each well. The cell plate was shaken for 1-2 minutes and then allowed to stand for 10 minutes. The signal value was then detected. The data were analyzed using XL-Fit, and the $IC_{50}$ of each compound was calculated.

4. The Assay Results were Shown in Table 3:

TABLE 3

Results of cell activity assay in vitro

| Compound | HT29 $IC_{50}$ (nM) |
|---|---|
| WX001A | 21 |
| WX001B | 26 |
| WX002 | 73 |
| WX003 | 69 |
| WX004 | 125 |
| WX005 | 49 |
| WX006 | 14 |
| WX007 | 11 |

Conclusion: The compounds of the present disclosure exhibit excellent activity of inhibiting the proliferation of HT29 cells.

Assay Example 3. Assay of In Vivo DMPK

In vivo DMPK assay in mouse

1. Purpose of the Assay:

Female BALB/c mice were used as assay animals to determine the blood concentration of compounds and evaluate the pharmacokinetic behavior after a single administration.

2. Procedure of the Assay:

Eight healthy adult female BALB/c mice were selected, wherein 4 mice were in the intravenous injection group and 4 mice were in the oral group. The vehicle in the intravenous injection group was 5% DMSO+95% (20% HP-β-CD). The compound to be assayed was mixed with an appropriate amount of vehicle for intravenous injection, vortexed and sonicated to prepare a clear solution of 0.5 mg/mL. The clear solution was filtered by a microporous membrane, and then ready for use. The vehicle in the oral group was 5% DMSO+95% (20% HP-β-CD). The compound to be assayed was mixed with the vehicle, vortexed and sonicated to prepare a solution of 0.3 mg/mL. Mice were administered 1 mg/kg intravenously or 3 mg/kg orally, and then whole blood was collected for a certain period. Plasma was prepared. The drug concentration was analyzed by LC-MS/MS method, and the pharmacokinetic parameters were calculated by Phoenix WinNonlin software (Pharsight, USA).

Note: DMSO: dimethyl sulfoxide; HP-β-CD: hydroxypropyl-β-cyclodextrin.

3. The Assay Results were Shown in Table 4:

TABLE 4

Results of PK assay of the compounds

| Compound | $C_{max}$ (nM) | F % | Oral DNAUC (nM · h/mpk) | $Vd_{ss}$ (L/kg) | Cl (mL/min/kg) | $T_{1/2}$ (h) |
|---|---|---|---|---|---|---|
| WX006 | 1400 | 70% | 1356 | 1.7 | 17.2 | 1.4 |
| WX007 | 595 | 46% | 1086 | 1.7 | 14.4 | 1.3 |

Note:

$C_{max}$ is maximum concentration; F % is oral bioavailability; DNAUC is $AUC_{PO}$/Dose, $AUC_{PO}$ is oral exposure, and Dose is drug dose; $Vd_{ss}$ is distribution volume; Cl is clearance rate; and $T_{1/2}$ is half-life.

Conclusion: The compounds of the present disclosure exhibit excellent oral exposure and bioavailability.

Assay Example 4. Assay of In Vivo Efficacy of Subcutaneous Xenograft Tumor of Human Colon Cancer HCT-116 Cells in BALB/c Nude Mouse Model 1. Purpose of the Assay:

The anti-tumor effect of WX007 was evaluated using a subcutaneous xenograft tumor model of human colon cancer HCT-116 cells in nude mouse.

2. Assay Animal:

Species: mouse

Strain: BALB/c nude mouse

Age: 6-8 weeks old

Gender: female

Weight: 17-23 grams

Vendor: Laboratory Animal Management Department, Shanghai Institute for Biomedical and Pharmaceutical Technologies Animal certificate number: 20180006020214

3. Assay Procedure:
   1) Assay cells and culture: Human colon cancer HCT-116 cells were cultured in monolayer in vitro. The culture conditions were McCoy's 5a medium plus 10% fetal bovine serum, and a 5% $CO_2$ incubator at 37° C. Routine digestion with trypsin-ethylene diamine tetraacetic acid was performed three times a week for passage. When the cell saturation was 80%-90% and the amount reached the requirement, the cells were harvested, counted, and inoculated;
   2) Tumor tissue inoculation and grouping: 0.2 mL ($5 \times 10^6$) of HCT-116 cells were subcutaneously inoculated into the right armpit of each mouse. When the average tumor volume reached 149 mm³, the animals were randomly divided into two groups and the administration was started. The grouping and administration schedule of the assay were shown in Table 5;

TABLE 5

Grouping and administration schedule of assay animals

| Group | Number of animals | Drug | Dosage (mg/kg) | Administration cycle | Route and frequency of administration |
|---|---|---|---|---|---|
| 1 | 6 | Solvent control (Vehicle) | — | 18 days | Oral administration (PO), once daily (QD) |
| 2 | 6 | WX007 | 15 | 18 days | Oral administration (PO), once daily (QD) |

3) Daily observation of assay animals: The development of this assay protocol and any modifications were evaluated and approved by the Institutional Animal Care and Use Committee (IACUC). The use and welfare of assay animals were carried out in accordance with the regulations of the Association for Assessment and Accreditation of Laboratory Animal Care (AAALAC). Animals were monitored daily for health and death. Routine examinations included observation of tumor growth and the effects of drug treatment on the animals' daily behavior such as behavioral activities, food and water intake (visual inspection only), weight changes (weight measurements twice a week), appearance signs or other abnormalities. Animal deaths and side effects in each group were recorded based on the number of animals in each group.
   4) Formulation of assay compound
   a) Vehicle group: corn oil.
   b) Assay compound group: A quantitative amount of the assay compound was weighed in a formulation bottle. A corresponding volume of corn oil was added and then the mixture was vortexed to obtain a clear solution. The compound was formulated once a week.
   5) Tumor measurement and assay indicator:
   a) Tumor diameter was measured twice a week with a vernier caliper. The calculation formula of tumor volume was: $TV = \frac{1}{2} \times a \times b^2$, wherein a and b represent the long and short diameters of tumor, respectively;
   b) The tumor-inhibitory efficacy of the compound was evaluated by TGI (%). TGI (%) reflected the inhibition rate of tumor growth. TGI (%) was calculated as follows: TGI (%)={[1−(average tumor volume at the end of administration of a treatment group−average tumor volume at the beginning of administration of the treatment group)]/(average tumor volume at the end of treatment in a solvent control group−average tumor volume at the beginning of treatment in the solvent control group)}×100%.

Figure 2:
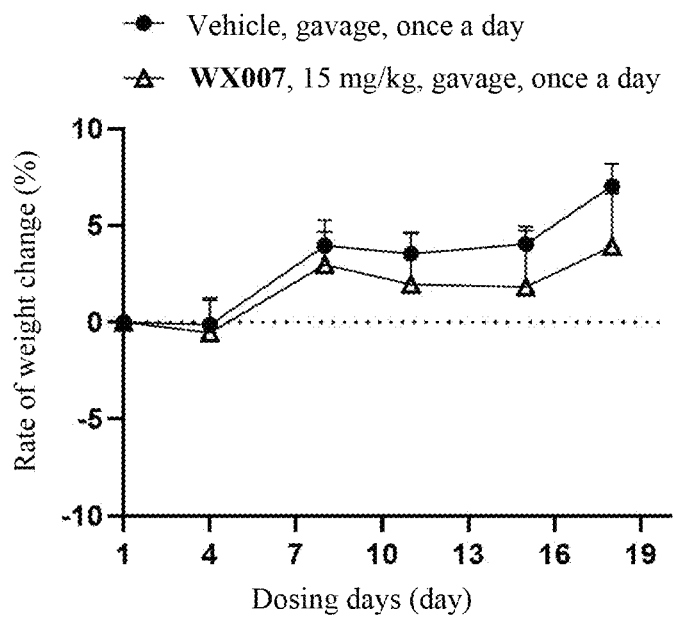
FIG. 2: Rate of weight change (%) in model animal of human colon cancer HCT116 during the administration.

4. Assay Results:
   1) As shown in Table 6 and FIG. 1, in the subcutaneous xenograft tumor model of human colon cancer HCT-116 cells in nude mouse, when administered orally to the 18th day, WX007 15 mg/kg in the administration group had a significant inhibitory effect on tumor growth with a TGI of 62%.
   2) The body weight of assay animals was used as a reference index for indirect determination of drug toxicity. As shown in FIG. 2, when administered to the 18th day, the body weight of all animals in the solvent control group and WX007 15 mg/kg administration group did not decrease significantly, and there was no morbidity or death.

TABLE 6

Results of in vivo efficacy assay in mouse HCT116 model

| Group | Drug | TGI |
|---|---|---|
| 2 | WX007 (15 mg/kg, PO, QD) | 62% |

Conclusion: The compounds of the present disclosure can significantly inhibit the growth of tumor. During the administration, the body weight of animals is not observed to decrease significantly, and the tolerance is good.

What is claimed is:
1. A compound of formula (III) or a pharmaceutically acceptable salt thereof,

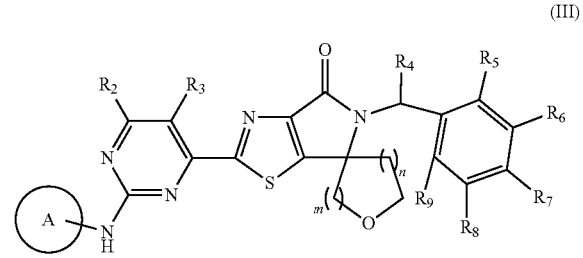

(III)

wherein
n is 0 or 1;
m is 1 or 2;
ring A is or $R_2$ and $R_3$ are each independently selected from H, F, Cl, Br, I, OH, CN, $NH_2$ and $C_{1-3}$ alkyl, wherein the $C_{1-3}$ alkyl is optionally substituted by 1, 2 or 3 $R_b$;
$R_4$ is H;
$R_5$, $R_6$, $R_7$, $R_8$ and $R_9$ are each independently selected from H, F, Cl, Br, I, OH, CN, $NH_2$ and $C_{1-3}$ alkyl, wherein the $C_{1-3}$ alkyl is optionally substituted by 1, 2 or 3 $R_c$; and $R_b$ and $R_c$ are each independently selected from F, Cl, Br, I, OH, CN and $NH_2$.

2. The compound or pharmaceutically acceptable salt thereof according to claim 1, wherein $R_2$ and $R_3$ are each independently selected from H, F, Cl, Br, I, OH, CN, $NH_2$ and $C_1$ alkyl wherein the $C_1$ alkyl is optionally substituted by 1, 2 or 3 $R_b$.

3. The compound or pharmaceutically acceptable salt thereof according to claim 2, wherein $R_2$ and $R_3$ are each independently selected from H and $CH_3$.

4. The compound or pharmaceutically acceptable salt thereof according to claim 1, wherein $R_5$, $R_6$, $R_7$, $R_8$ and $R_9$ are each independently selected from H, F, Cl, Br, I, OH, CN, $NH_2$, and $C_{1-2}$ alkyl, wherein the $C_{1-2}$ alkyl are optionally substituted by 1, 2 or 3 $R_c$.

5. The compound or pharmaceutically acceptable salt thereof according to claim 4, wherein $R_5$, $R_6$, $R_7$, $R_8$ and $R_9$ are each independently selected from H, F, Cl, Br, I, OH, CN and $NH_2$.

6. The compound or pharmaceutically acceptable salt thereof according to claim 1, wherein the structural moiety

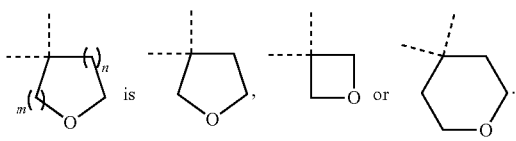

7. The compound or pharmaceutically acceptable salt thereof according to claim 1, wherein the compound is

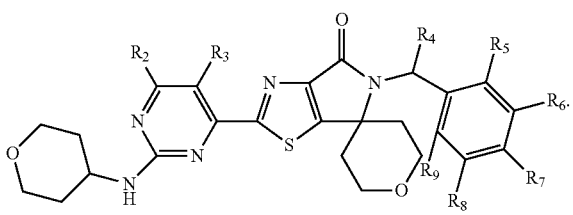

8. The compound or pharmaceutically acceptable salt thereof according to claim 1, wherein the compound is

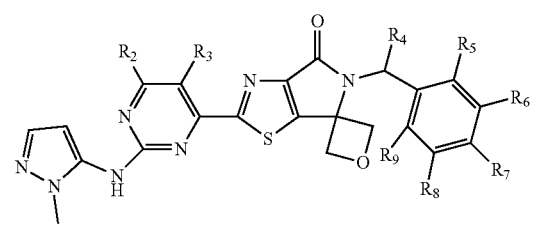

or

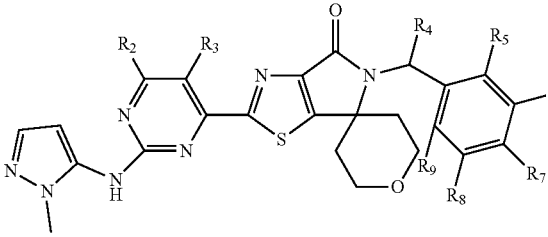

9. The compound or pharmaceutically acceptable salt thereof according to claim 1, wherein the compound is

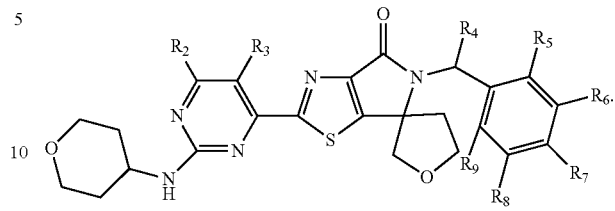

10. The compound or pharmaceutically acceptable salt thereof according to claim 1, wherein the compound is

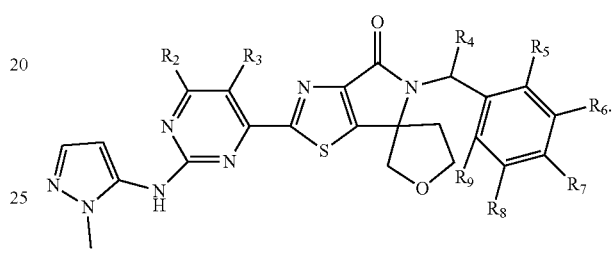

11. A compound represented by the following formula or a pharmaceutically acceptable salt thereof,

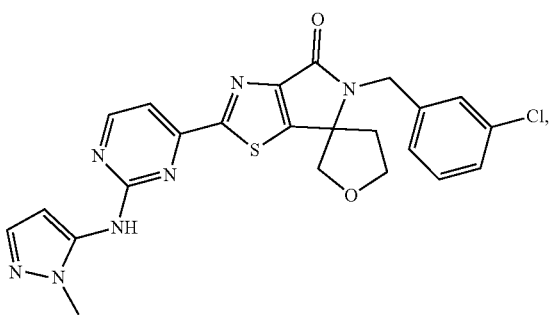

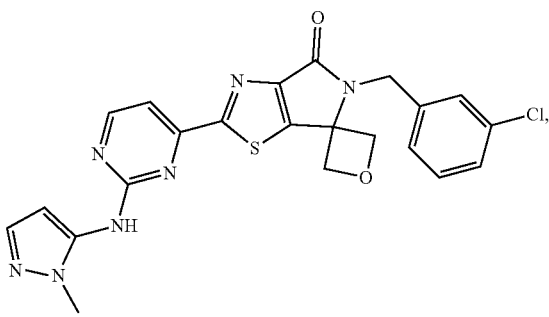

-continued
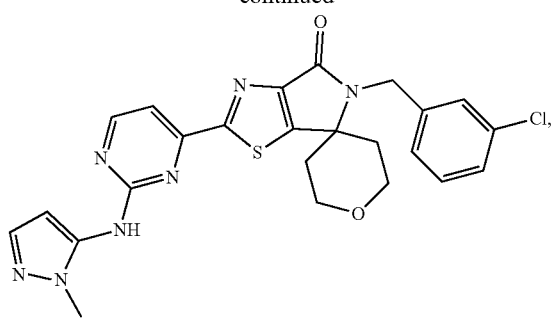
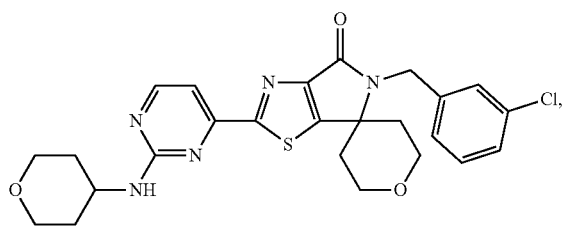
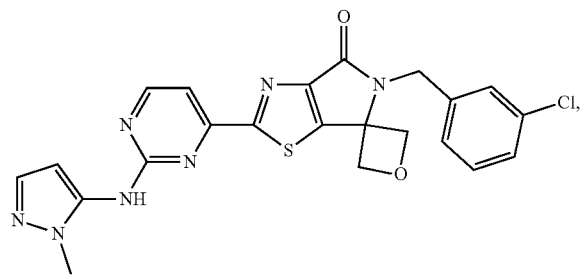
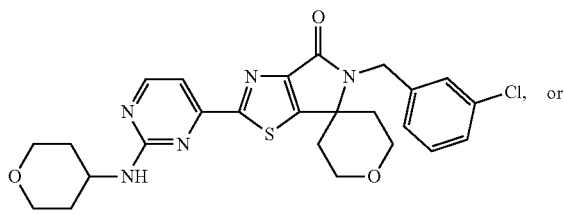
-continued
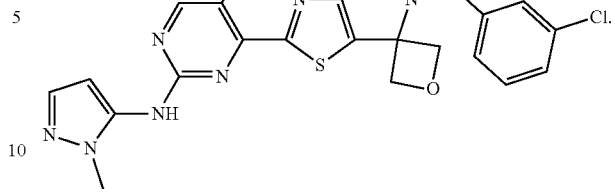
12. The compound or pharmaceutically acceptable salt thereof according to claim 11, wherein the compound is
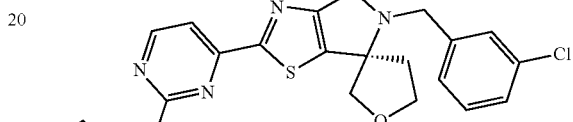
, or
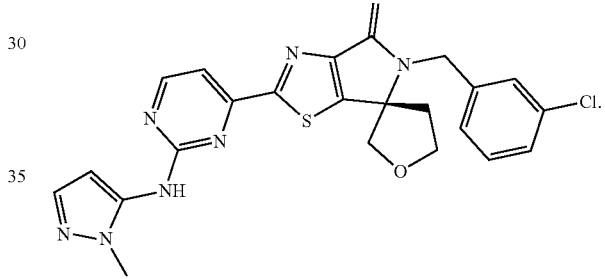
13. A medicament, comprising the compound or pharmaceutically acceptable salt thereof according to claim 1.
14. A medicament, comprising the compound or pharmaceutically acceptable salt thereof according to claim 11.
* * * * *